United States Patent
Nejadnik

(10) Patent No.: US 12,121,544 B2
(45) Date of Patent: Oct. 22, 2024

(54) CELL THERAPIES AND METHODS OF TREATMENT FOR SMALL-VOLUME STROKE

(71) Applicant: SanBio, Inc., Mountain View, CA (US)

(72) Inventor: Bijan Nejadnik, Burlingame, CA (US)

(73) Assignee: SanBio, Inc., Oakland, CA (US)

( * ) Notice: Subject to any disclaimer, the term of this patent is extended or adjusted under 35 U.S.C. 154(b) by 0 days.

(21) Appl. No.: 17/664,856

(22) Filed: May 24, 2022

(65) Prior Publication Data

US 2022/0387506 A1 Dec. 8, 2022

Related U.S. Application Data

(60) Provisional application No. 63/194,021, filed on May 27, 2021.

(51) Int. Cl.
*A61K 35/28* (2015.01)
*A61K 9/00* (2006.01)
*A61P 9/10* (2006.01)

(52) U.S. Cl.
CPC ............ *A61K 35/28* (2013.01); *A61K 9/0085* (2013.01); *A61P 9/10* (2018.01)

(58) Field of Classification Search
None
See application file for complete search history.

(56) References Cited

U.S. PATENT DOCUMENTS

| | | | |
|---|---|---|---|
| 5,486,359 A | 1/1996 | Caplan et al. | |
| 6,534,261 B1 | 3/2003 | Cox et al. | |
| 6,607,882 B1 | 8/2003 | Cox, III et al. | |
| 6,785,613 B2 | 8/2004 | Eisenberg et al. | |
| 6,794,136 B1 | 9/2004 | Eisenberg et al. | |
| 6,824,978 B1 | 11/2004 | Cox, III et al. | |
| 6,979,539 B2 | 12/2005 | Cox, III et al. | |
| 7,013,219 B2 | 3/2006 | Case et al. | |
| 7,026,462 B2 | 4/2006 | Rebar et al. | |
| 7,067,317 B2 | 6/2006 | Rebar et al. | |
| 7,177,766 B2 | 2/2007 | Eisenberg et al. | |
| 7,220,719 B2 | 5/2007 | Case et al. | |
| 7,560,440 B2 | 7/2009 | Rebar et al. | |
| 7,605,140 B2 | 10/2009 | Rebar et al. | |
| 7,682,825 B2 * | 3/2010 | Dezawa | A61P 25/28 435/375 |
| 7,788,044 B2 | 8/2010 | Eisenberg et al. | |
| 8,071,564 B2 | 12/2011 | Rebar et al. | |
| 8,092,792 B2 | 1/2012 | Dezawa et al. | |
| 10,245,286 B2 | 4/2019 | Dao et al. | |
| 11,577,062 B2 * | 2/2023 | Katz | A61K 35/28 |
| 2003/0003090 A1 | 1/2003 | Prockop et al. | |
| 2004/0208858 A1 * | 10/2004 | Tennekoon | C12N 5/0618 435/368 |
| 2010/0266554 A1 | 10/2010 | Mori et al. | |
| 2011/0229442 A1 | 9/2011 | Dezawa | |
| 2011/0268710 A1 * | 11/2011 | Sanberg | A61K 35/14 514/8.4 |
| 2013/0195817 A1 * | 8/2013 | Dao | A61P 9/10 424/93.21 |
| 2019/0167730 A1 | 6/2019 | Dao et al. | |
| 2019/0290846 A1 | 9/2019 | McGrogan | |

FOREIGN PATENT DOCUMENTS

| | | |
|---|---|---|
| WO | WO 2005/100552 | 10/2005 |
| WO | WO 2009/023251 | 2/2009 |
| WO | WO 2018/125829 | 7/2018 |
| WO | WO 2022/251829 | 12/2022 |

OTHER PUBLICATIONS

Aizman et al., "Comparison of the neuropoietic activity of gene-modified versus parental mesenchymal stromal cells and the identification of soluble and extracellular matrix-related neuropoietic mediators," Stem Cell Res Ther, 5(1):29:1-15 (Feb. 26, 2014).
Aizman et al., "Extracellular Matrix Produced by Bone Marrow Stromal Cells and by Their Derivatne, SB623 Cells, Supports Neural Cell Growth," J Neurosci. Res. 87(14):3198-3206 (2009).
Artavanis-Tsakonas et al., "Notch Signaling," Science, 268(5208):225-232 (1995).
Bliss et al. Cell transplantation therapy for stroke. Stroke. 2007; 38 (Part 2): 817-826.
Campagnoli et al., "Identification of Mesenchymal Stem/Progenitor Cells in Human Firsttrimester Fetal Blood, Liver, and Bone Marrow," Blood, 98(8):2396-2402 (2001).
Dao et al., "Comparing the angiogenic potency of naïve marrow stromal cells and Notch-transfected marrow stromal cells," J Translational Medicine, 11:81-91 (2013).
Del Amo, F. et al., "Cloning, Analysis and Chromosomal Localization of Notch-I, a Mouse Homolog of *Drosophilia* Notch," Genomics, 12:259-264 (1993).
Dezawa et al. "Sciatic Nerve Regeneration in Rats Induced by Transplantation of in Vitro Differentiated Bone-Marrow Stromal Cells," The European Journal of Neuroscience 14(11):1771-1776 (2001).
Dezawa et al., "Specific Induction of Neuronal Cells From Bone Marrow Stromal Cells and Application for Autologous Transplantation," J Clin Invest 113(12):1701-1710 (2004).
Dobkin B.H. Strategies for stroke rehabilitation. Lancet Neurol. 2004;3(9):528-536.
Ehebauer et al., "Notch Signaling Pathway," Sci. STKE, 2006(364):cm7 (2006).
Erices et al., "Mesenchymal Progenitor Cells in Human Umbilical Cord Blood," Br. J Haematol., 109(1):235-242 (2000).
Fisher et al., "Identifying and utilizing the ischemic penumbra", Neurology, 79 (Suppl. 1): S79-S85, 2012.

(Continued)

*Primary Examiner* — Blaine Lankford
(74) *Attorney, Agent, or Firm* — Levine Bagade Han LLP

(57) ABSTRACT

Disclosed are methods of treating a subject following a small-volume ischemic stroke suffered by the subject and methods of treating a subject with a stroke-induced motor deficit. Disclosed also is a composition for treating small-volume ischemic stroke. In one aspect, the method of treating a subject following a small-volume ischemic stroke comprises administering, to a brain region surrounding a small-volume ischemic core of the subject, a therapeutically effective amount of cells, wherein the cells are descended from mesenchymal stem cells transiently-transfected by a polynucleotide encoding a Notch intracellular domain.

20 Claims, 7 Drawing Sheets

(56) References Cited

OTHER PUBLICATIONS

Hou et al., "Induction of Umbilical Cord Blood Mesenchymal Stem Cells Into Neuron-Like Cells in Vitro," Int. J Hematol., 78(3):256-261 (2003).
Jiang et al., "Pluripotency of Mesenchymal Stem Cells Derived From Adult Marrow," Nature 418:41-49 (2002).
Johnson, Walter et al., Stroke: A global response is needed. Bulletin of the World Health Organization. Sep. 2016; vol. 94(9): 634.
Mumm et al., "Notch Signaling: From the Outside in," Dev. Bioi., 228(2):151-165 (2000).
Pittenger et al., "Multilineage Potential of Adult Human Mesenchymal Stem Cells," Science 284(5411):143-147 (1999).
Prockop et al., "Marrow Stromal Cells as Stem Cells for Nonhematopoietic Tissues," Science 276(5309):71-74 (1997).
Savitz et al. Cell therapy for stroke. NeuroRx. 2004; 1(4): 406-414.
Schroeter et al., "Notch-1 Signalling Requires Ligand-Induced Proteolytic Release of Intracellular Domain," Nature, 393:382-386 (1998).
Vincent et al., "Gene therapy progress and prospects: therapeutic angiogenesis for ischemic cardiovascular disease", Gene Therapy, 14:781-789, 2007.
Weinmaster et al., "A Homolog of *Drosophila* Notch Expressed During Mammalian Development," Development 113:199-205 (1991).
Bates et al., "A Double-Blind, Controlled Phase 2b Study of the Safety and Efficacy of Modified Stem Cells (SB623) in Patients with Chronic Motor Deficit from Ischemic Stroke," SanBio Incorporated Clinical Protocol, pp. 1-86, Jan. 5, 2017, retrieved from the internet: <URL:https://www.clinicaltrials.gov/ProvidedDocs/41/NCT02448641/Pro_000.pdf> on Sep. 2, 2022.
Khoury et al., "Visual assessment of diffusion weighted imaging infarct vol. lacks accuracy and reliability," Journal of Neurointerventional Surgery, vol. 11, No. 9, pp. 947-954, Feb. 2, 2019.
Steinberg, Gary K. et al., "Clinical Outcomes of Transplanted Modified Bone Marrow-Derived Mesenchymal Stem Cells in Stroke, A Phase 1/2a Study," *Stroke,* 47: 1817-1824, 2016. Doi: 10.1161/STROKEAHA.116.012995.
"Vandefitemcel", WHO Drug Information, vol. 31, No. 1, pp. 142-143, 2017.

\* cited by examiner

Subject Condition, Stroke Location, and Week 24 Delta Rates by Population Percentage

| Point | Pop. % | Treatment # (n) | Control # (n) | FMMS Base-line | MRS Base-line | Vol. of Stroke | Sub-cortical white matter | Sub-cortical grey matter | Frontal | Parietal | Temporal | Delta FMMS Change | Delta MRS Change | Delta Comp. Res. Rate | p-value of Delta Comp. Res. Rate |
|---|---|---|---|---|---|---|---|---|---|---|---|---|---|---|---|
| P1 | 9% | 9 | 6 | - | Low | Low | - | No | No | - | - | 5.33 | 0 | 1 | 0 |
| P2 | 11% | 13 | 5 | - | Low | Low | - | - | - | No | - | 2.75 | -0.2 | 0.85 | 0 |
| P3 | 25% | 24 | 16 | High | - | Low | - | - | - | - | No | 5.63 | -0.25 | 0.58 | 0 |
| P4 | 31% | 36 | 14 | - | - | Low | - | - | - | No | No | 4.02 | -0.04 | 0.51 | 0 |
| P5 | 47% | 51 | 26 | - | - | Low | - | - | - | - | - | 1.9 | -0.04 | 0.3 | 0.02 |
| P6 | 51% | 62 | 21 | - | - | - | Yes | - | - | No | - | 0.82 | 0 | 0.23 | 0.05 |
| P7 | 63% | 70 | 32 | - | - | - | - | - | - | - | - | 0.63 | 0.01 | 0.05 | 0.77 |
| P8 | 79% | 77 (low cell processing time) | 51 (low cell processing time) | - | - | - | - | - | - | - | - | 1.36 | -0.11 | 0.09 | 0.40 |
| P9 | 97% | 107 | 51 | - | - | - | - | - | - | - | - | 0.77 | -0.03 | 0.08 | 0.43 |

FIG. 6

CELL THERAPIES AND METHODS OF TREATMENT FOR SMALL-VOLUME STROKE

CROSS-REFERENCE TO RELATED APPLICATION

This application claims the benefit of U.S. Provisional Application No. 63/194,021 filed on May 27, 2021, the content of which is incorporated herein by reference in its entirety.

TECHNICAL FIELD

The present disclosure relates generally to the field of regenerative cell therapies, and, more specifically, to cell therapies and methods of treatment for small-volume stroke.

BACKGROUND

Worldwide, stroke is the second leading cause of death and the third leading cause of disability [1]. After an ischemic stroke, the acute period is generally defined from hours to several days after the stroke event or incident. Immediate post-stroke interventions for acute ischemic stroke focus on life support through respiratory and cardiac control of blood pressure, monitoring oxygen saturation and blood glucose levels, prevention of metabolic disturbances, maintenance of organ function, and management of elevated intracranial pressure.

One of the only approved therapies for acute ischemic stroke in the United States are thrombolytic agents, to be given to the patient within 3 hours of the onset of the stroke. Some studies have estimated that less than 5% of acute ischemic stroke subjects actually receive this therapy, likely due to the stringent criteria for thrombolytic intervention, the lack of adequate facilities, and the subject arriving beyond the 3-hour window [2]. Approximately 70% to 85% of patients that suffer their first stroke develop hemiplegia or at least some paralysis on one side of the patient's body. Six months following the stroke event or incident, only 60% of patients who develop hemiparesis and need inpatient rehabilitative care have achieved functional independence in performing simple daily activities [3].

Once a stroke patient has entered the chronic phase, generally defined as more than several months after the stroke event or incident, physical therapy is often the patient's only prescribed rehabilitative regimen. For these chronic-stroke patients, no proven biological or pharmaceutical therapies have been shown to significantly reverse the damage and improve the patients' motor functions. While a variety of cellular therapies have been proposed and studied, clinical trials for these therapies have so far been limited with the patients in such trials only showing modest improvements [4-6]. Moreover, no investigation has been made as to whether certain therapies are more effective at treating particular patient sub-populations such as stroke patients with differing ischemic core sizes or volumes.

Therefore, there is a need for a safe and effective therapy for the treatment of chronic stroke patients or those patients suffering from chronic stroke-induced motor deficits.

SUMMARY

Disclosed are methods of treating a subject following a small-volume ischemic stroke suffered by the subject and methods of treating a subject with a stroke-induced motor deficit. Disclosed also is a composition for treating small-volume ischemic stroke.

In one aspect, a method of treating a subject following a small-volume ischemic stroke comprises administering, to a brain region surrounding a small-volume ischemic core of the subject, a therapeutically effective amount of cells. The cells can be descended from mesenchymal stem cells transiently-transfected by a polynucleotide encoding a Notch intracellular domain (NICD).

The cells can be made by a method comprising providing a culture of the mesenchymal stem cells, contacting the culture of mesenchymal stem cells with a polynucleotide encoding the NICD, selecting cells that comprise the polynucleotide, and further culturing the selected cells in the absence of selection for the polynucleotide. The mesenchymal stem cells can be human bone marrow-derived cells. Moreover, the polynucleotide encoding the NICD does not encode a full-length Notch protein.

The small-volume ischemic core can be an ischemic core having an ischemic core volume of less than 50 cubic centimeters (cc). For example, the small-volume ischemic core can be an ischemic core having an ischemic core volume of between about 2 cc and 50 cc.

In some instances, the treatment is especially effective when the small-volume ischemic core is located in a region of the brain of the subject other than a parietal region such as a cortical frontal region, a cortical temporal region, a subcortical white matter, or a subcortical grey matter of the brain of the subject.

In some instances, the treatment is effective even when the small-volume ischemic stroke occurred more than six months prior to administering the cells. For example, the treatment can be effective even when the small-volume ischemic stroke occurred between six months and 90 months prior to administering the cells.

The step of administering the therapeutically effective amount of the cells can comprise injecting a cell suspension comprising the cells at deposit sites within the brain of the subject. The cell suspension can comprise the cells suspended in a sterile isotonic crystalloid solution.

The step of administering the therapeutically effective amount of the cells can further comprise injecting at least part of the cell suspension comprising the cells at one or more deposit sites at an outer periphery of an ischemic penumbra or chronic ischemic penumbra surrounding the small-volume ischemic core. For example, the step of administering the therapeutically effective amount of the cells can comprise injecting at least part of the cell suspension comprising the cells at one or more deposit sites proximal to the ischemic penumbra or the chronic ischemic penumbra surrounding the small-volume ischemic core.

The step of administering the therapeutically effective amount of the cells can further comprise injecting at least part of the cell suspension comprising the cells at one or more deposit sites within the ischemic penumbra or the chronic ischemic penumbra surrounding the small-volume ischemic core. In some instances, the step of administering the therapeutically effective amount of the cells can comprise injecting at least part of the cell suspension comprising the cells at one or more deposit sites distal to the ischemic penumbra/chronic ischemic penumbra or within the small-volume ischemic core.

The step of administering the therapeutically effective amount of the cells can further comprise administering the therapeutically effective amount of the cells stereotactically via a single burr-hole craniostomy.

The therapeutically effective amount of cells can be approximately 2.5 million cells (or 2.5 million cells±0.1 million cells). The step of administering the approximately 2.5 million cells can comprise injecting a cell suspension comprising the cells at five deposit sites along a first deposit track or needle track, five deposit sites along a second deposit track or needle track, and five deposit sites along a third deposit track or needle track. Approximately 20-µL of the cell suspension can be injected at each deposit site. The cell suspension can have a cell concentration of approximately $8.5*10^6$ cells/mL.

The therapeutically effective amount of cells can also be approximately 5.0 million cells (or 5.0 million cells±0.1 million cells). The step of administering the approximately 5.0 million cells can comprise injecting a cell suspension comprising the cells at five deposit sites along a first deposit track or needle track, five deposit sites along a second deposit track or needle track, and five deposit sites along a third deposit track or needle track. Approximately 20-µL of the cell suspension can be injected at each deposit site. The cell suspension can have a cell concentration of approximately $17.0*10^6$ cells/mL.

The method can further comprise subjecting a formulated dose of the cells to post-release testing prior to administering the cells to the subject.

The method can further comprise determining a degree of disability of the subject by determining an mRS score of the subject and administering the therapeutically effective amount of cells only when the mRS score of the subject is between 2 and 4.

Also disclosed is a method of treating a subject with a stroke-induced motor deficit. The method can comprise determining a volume of an ischemic core of the subject and administering, to a brain region surrounding the ischemic core of the subject, a therapeutically effective amount of cells only when the volume of the ischemic core is determined to be less than 50 cubic centimeters (cc). For example, the method can comprise administering, to the brain region surrounding the ischemic core of the subject, the therapeutically effective amount of cells only when the volume of the ischemic core is between about 2 cc and 50 cc.

The stroke-induced motor deficit can be the result of an ischemic stroke suffered by the subject. In some instances, the ischemic stroke occurred more than six months prior to administering the cells. For example, the small-volume ischemic stroke occurred between six months and 90 months prior to administering the cells.

In certain instances, the method comprises administering, to the brain region surrounding the ischemic core of the subject, the therapeutically effective amount of cells only when the ischemic stroke occurred more than six months prior (e.g., between six months and 90 months prior).

The cells can be descended from mesenchymal stem cells transiently-transfected by a polynucleotide encoding a Notch intracellular domain (NICD).

The cells can be made by a method comprising providing a culture of the mesenchymal stem cells, contacting the culture of mesenchymal stem cells with a polynucleotide encoding the NICD, selecting cells that comprise the polynucleotide, and further culturing the selected cells in the absence of selection for the polynucleotide. The mesenchymal stem cells can be human bone marrow-derived cells. Moreover, the polynucleotide encoding the NICD does not encode a full-length Notch protein.

In certain instances, the method comprises administering, to the brain region surrounding the ischemic core of the subject, the therapeutically effective amount of cells only when the ischemic core is located in a region of the brain of the subject other than a parietal region. For example, the method can comprise administering, to the brain region surrounding the ischemic core of the subject, the therapeutically effective amount of cells only when part of the ischemic core is located in at least one of a cortical frontal region, a cortical temporal region, a subcortical white matter, and a subcortical grey matter of the brain of the subject.

The step of administering the therapeutically effective amount of the cells can comprise injecting a cell suspension comprising the cells at deposit sites within the brain of the subject. The cell suspension can comprise the cells suspended in a sterile isotonic crystalloid solution.

The step of administering the therapeutically effective amount of the cells can further comprise injecting at least part of the cell suspension comprising the cells at one or more deposit sites at an outer periphery of an ischemic penumbra or chronic ischemic penumbra surrounding the small-volume ischemic core. For example, the step of administering the therapeutically effective amount of the cells can comprise injecting at least part of the cell suspension comprising the cells at one or more deposit sites proximal to the ischemic penumbra or chronic ischemic penumbra surrounding the small-volume ischemic core. The step of administering the therapeutically effective amount of the cells can also comprise injecting at least part of the cell suspension comprising the cells at one or more deposit sites within the ischemic penumbra or chronic ischemic penumbra surrounding the small-volume ischemic core. In some instances, the step of administering the therapeutically effective amount of the cells can comprise injecting at least part of the cell suspension comprising the cells at one or more deposit sites distal to the ischemic penumbra/chronic ischemic penumbra or within the small-volume ischemic core.

The step of administering the therapeutically effective amount of the cells can further comprise administering the therapeutically effective amount of the cells stereotactically via a single burr-hole craniostomy.

The therapeutically effective amount of cells can be approximately 2.5 million cells (or 2.5 million cells±0.1 million cells). The step of administering the approximately 2.5 million cells can comprise injecting a cell suspension comprising the cells at five deposit sites along a first deposit track or needle track, five deposit sites along a second deposit track or needle track, and five deposit sites along a third deposit track or needle track. Approximately 20-µL of the cell suspension can be injected at each deposit site. The cell suspension can have a cell concentration of approximately $8.5*10^6$ cells/mL.

The therapeutically effective amount of cells can also be approximately 5.0 million cells (or 5.0 million cells±0.1 million cells). The step of administering the approximately 5.0 million cells can comprise injecting a cell suspension comprising the cells at five deposit sites along a first deposit track or needle track, five deposit sites along a second deposit track or needle track, and five deposit sites along a third deposit track or needle track. Approximately 20-µL of the cell suspension can be injected at each deposit site. The cell suspension can have a cell concentration of approximately $17.0*10^6$ cells/mL.

The method can further comprise subjecting a formulated dose of the cells to post-release testing prior to administering the cells to the subject.

The method can further comprise determining a degree of disability of the subject by determining an mRS score of the subject and administering the therapeutically effective amount of cells only when the mRS score of the subject is between 2 and 4.

Also disclosed is a composition for treating small-volume ischemic stroke. The composition can comprise a therapeutically effective amount of cells and a pharmaceutically acceptable carrier or diluent. The cells can be descended from mesenchymal stem cells transiently-transfected by a polynucleotide encoding a Notch intracellular domain (NICD).

The cells can be made by a method comprising providing a culture of the mesenchymal stem cells, contacting the culture of mesenchymal stem cells with a polynucleotide encoding the NICD, selecting cells that comprise the polynucleotide, and further culturing the selected cells in the absence of selection for the polynucleotide. The mesenchymal stem cells can be transiently-transfected with a plasmid comprising the polynucleotide encoding the NICD.

The mesenchymal stem cells can be human bone marrow-derived cells. Moreover, the polynucleotide encoding the NICD does not encode a full-length Notch protein.

The pharmaceutically acceptable carrier or diluent can comprise a sterile isotonic crystalloid solution (e.g., Plasma-Lyte A). The composition can be a cell suspension packaged in a sealed vial prior to being administered.

The therapeutically effective amount of cells can be approximately 2.5 million cells. When the therapeutically effective amount of cells is approximately 2.5 million cells, the composition can be an approximately 0.3 mL cell suspension with a cell concentration of approximately $8.5*10^6$ cells/mL.

The therapeutically effective amount of cells can also be approximately 5.0 million cells. When the therapeutically effective amount of cells is approximately 2.5 million cells, the composition can be an approximately 0.3 mL cell suspension with a cell concentration of approximately $17.0*10^6$ cells/mL.

In some instances, the therapeutically effective amount of cells can be between approximately 2.0 million cells and approximately 5.0 million cells.

Also disclosed is the use of cells in the manufacture of a medicament for treating a subject following a small-volume ischemic stroke suffered by the subject, comprising: administering to a brain region surrounding a small-volume ischemic core of the subject a therapeutically effective amount of cells, wherein the cells are descended from mesenchymal stem cells transiently-transfected by a polynucleotide encoding a Notch intracellular domain (NICD).

Further disclosed is the use of cells in the manufacture of a medicament for treating a subject with a stroke-induced motor deficit, comprising: determining a volume of an ischemic core of the subject; and administering, to a brain region surrounding the ischemic core of the subject, a therapeutically effective amount of cells only when the volume of the ischemic core is determined to be less than 50 cubic centimeters (cc), wherein the cells are descended from mesenchymal stem cells transiently-transfected by a polynucleotide encoding a Notch intracellular domain (NICD).

Also disclosed are cells descended from mesenchymal stem cells transiently-transfected by a polynucleotide encoding a Notch intracellular domain (NICD) for use in a method of treating a subject following a small-volume ischemic stroke suffered by the subject, wherein the method comprises administering, to a brain region surrounding a small-volume ischemic core of the subject, a therapeutically effective amount of the cells.

Further disclosed are cells descended from mesenchymal stem cells transiently-transfected by a polynucleotide encoding a Notch intracellular domain (NICD) for use in a method of treating a subject with a stroke-induced motor deficit, wherein the method comprises: determining a volume of an ischemic core of the subject; and administering, to a brain region surrounding the ischemic core of the subject, a therapeutically effective amount of cells only when the volume of the ischemic core is determined to be less than 50 cubic centimeters (cc), wherein the cells are descended from mesenchymal stem cells transiently-transfected by a polynucleotide encoding a Notch intracellular domain (NICD).

BRIEF DESCRIPTION OF THE DRAWINGS

FIG. 6 is a table comprising information concerning the stroke location, baseline characteristics, and delta response rates of the study population broken down by population percentage

DETAILED DESCRIPTION

Figure 1:
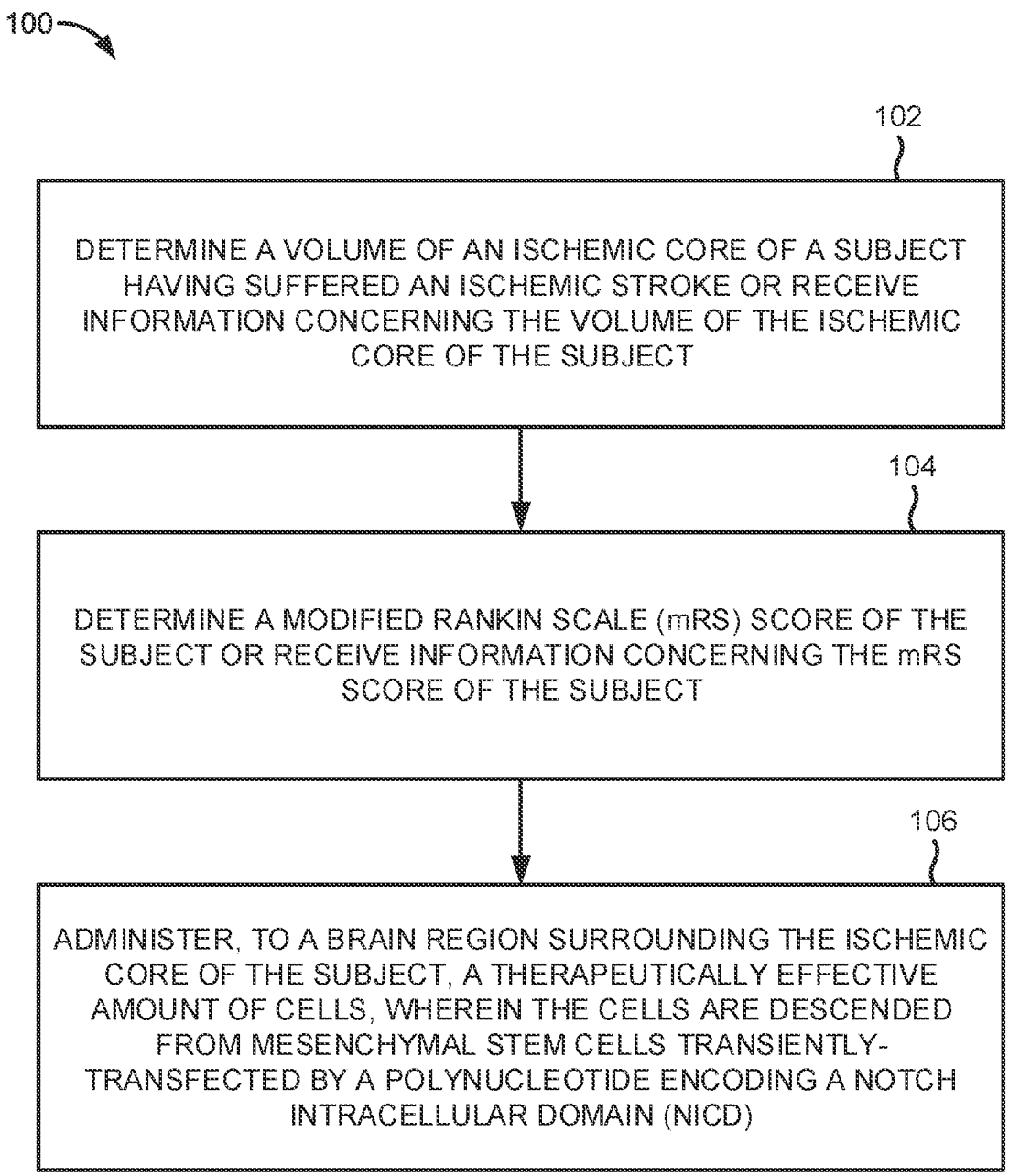
FIG. 1 illustrates a method of treating a subject with a stroke-induced motor deficit.

The below terms are defined as follows for purposes of this disclosure.

Definitions

"Angiogenesis" or "angiogenic" refers to the formation of new vasculature (e.g., blood vessels; e.g., veins, arteries, venules, arterioles, capillaries). Angiogenesis can occur by sprouting of new vessels from an existing vessel, and/or by in situ coalescence of endothelial cells to form new blood vessels. Angiogenesis also includes the attendant processes of matrix remodeling and cell recruitment (e.g., recruitment of smooth muscle cells, monocytes and/or pericytes). Angiogenesis further includes proliferation and/or migration of endothelial cells.

The terms "DNTT-MSCs" ("descendants of NICD transiently-transfected MSCs") and "SB623 cells" (with the International Nonproprietary Name—or generic name—vandefitemcel) refer to populations of cells obtained following transient expression of an exogenous Notch intracellular domain (NICD) in MSCs. For example, a population of DNTT-MSCs can be obtained by transient transfection of MSCs with a vector comprising sequences encoding a NICD (e.g., from the human Notch 1 protein) but not encoding a full-length Notch protein followed by selection (e.g., with G418). The selected cells can be further cultured in a standard culture medium, optionally supplemented with a serum, in the absence of any added growth factors or differentiation factors (other than those which may be present in the serum, if serum is present in the culture medium). DNTT-MSCs can be derived from human bone marrow MSCs by transient transfection of human bone marrow MSCs with NICD (e.g., the human Notch1 intracellular domain (NICD1)), followed by selection, and subsequent expansion. This process produces a cell population that demonstrates superior angiogenic and neuropoietic properties in vitro, compared to the parental MSCs [7-9]. The neuropoietic effects of DNTT-MSCs have been attributed to the increased expression, and correspondingly, increased secretion, of FGF1, FGF2, and BMPs [7, 9].

"Fugl-Meyer Assessment" or "FMA" is an index or scale used to assess the sensorimotor impairment in individuals who have had a stroke. The FMA index or scale is applied clinically to determine impairment severity, assess motor recovery, and plan treatment. The FMA index or scale was first proposed by Axel Fugl-Meyer and his colleagues in 1975 as a standardized assessment for post-stroke recovery [10]. The assessment is made in five domains, including: (1) motor function (upper extremity and lower extremity motor function); (2) sensory function; (3) balance; (4) joint range of motion; and (5) joint pain. A total of 155 items are assessed with a maximum score of 226 points across all five domains.

"Fugl-Meyer Motor Scale or Score" or "FMMS" is a subscale used to assess the motor functioning or impairment of individuals who have had a stroke including range of motion in both the upper and lower limbs. The FMMS ranges from 0 points (hemiplegia) to 100 points (normal motor performance). The FMMS maximum score of 100 points accounts for almost half of the maximum total FMA score (226 points) across all five domains. The FMMS maximum score is divided into 66 points for the upper extremity (based on an evaluation of 33 items) and 34 points for the lower extremity (based on an evaluation of 17 items).

"FMMS Upper Extremity" or "FMMS UE" is a more specific subscale used to assess the motor functioning of the upper extremity or upper limbs of individuals who have had a stroke.

"FMMS Lower Extremity" or "FMMS LE" is a more specific subscale used to assess the motor functioning of the lower extremity or lower limbs of individuals who have had a stroke.

The terms "implantation" and "transplantation" are used to denote the introduction of exogenous cells into a subject or patient. Exogenous cells can be autologous (i.e. obtained from the subject) or allogeneic (i.e., obtained from an individual other than the subject).

"Mesenchymal cells" refer to cells of mesenchymal tissue (e.g., chondroblasts, chondrocytes, osteoblasts, osteocytes, adipocytes) and their precursors and include, for example, fibroblasts (e.g., human foreskin fibroblasts), MSCs (as defined herein) and cells derived from MSCs such as, for example, DNTT-MSCs, as defined herein.

"Minimally Clinically Important Difference" or "MCID" is the smallest change in a treatment outcome that a patient or individual would perceive or identify as meaningful or important. For example, an MCID as it relates to FMA can be the smallest change in a score used to evaluate a stroke patient in one or more of the five FMA domains. As a more specific example, an MCID threshold for evaluating a stroke treatment can require that a stroke patient exhibit an improvement of at least 6 points in their FMMS UE score from a baseline measurement.

"Modified Rankin Scale" or "mRS" is a clinician-reported ordinal scale used to measure the degree of disability or disability level of patients who have had a stroke. The scale ranges from a grade or score of 0 (no symptoms at all) to 6 (death). Those with a grade or score of 1 have no significant disability and are able to carry out all usual duties and activities. Those with a grade or score of 2 have a slight disability and are unable to perform all previous activities but are able to look after their own affairs without assistance. Those with a grade or score of 3 are moderately disabled, require some help, but are able to walk without assistance. Those with a grade or score of 4 exhibit moderately severe disability and are unable to walk and unable to attend to their own bodily needs without assistance. Those with a grade or score of 5 are severely disabled, bedridden, and incontinent and require constant nursing care and attention.

"MSCs" ("mesenchymal stem cells") refer to adherent, non-hematopoietic pluripotent cells obtained from bone marrow. These cells are variously known as mesenchymal stem cells, mesenchymal stromal cells, marrow adherent stromal cells, marrow adherent stem cells and bone marrow stromal cells. MSCs can also be obtained from, e.g., umbilical cord blood, adipose tissue, dental pulp, Wharton's jelly, and various types of connective tissue. MSCs can be obtained by selecting (e.g., by growth in culture) adherent cells (i.e., cells that adhere to tissue culture plastic) from bone marrow. To obtain MSC populations having a sufficient number of cells for use in therapy, populations of adherent cells are expanded in culture after selecting for adherence. Expansion in culture also enriches for MSCs, since contaminating cells (such as monocytes) do not proliferate under the culture conditions.

Exemplary disclosures of MSCs are provided in U.S. Patent Publication No. 2003/0003090; Prockop (1997) Science 276:71-74 and Jiang (2002) Nature 418:41-49. Methods for isolating and purifying MSCs can be found, for example, in U.S. Pat. No. 5,486,359; Pittenger et al. (1999) Science 284:143-147 and Dezawa et al. (2001) Eur. J. Neurosci. 14:1771-1776. Human MSCs are commercially available (e.g., BioWhittaker, Walkersville, Md.) or can be obtained from donors by, e.g., bone marrow aspiration, followed by culture and selection for adherent bone marrow cells. See, e.g., WO 2005/100552.

MSCs can also be isolated from umbilical cord blood. See, for example, Campagnoli et al. (2001) Blood 98:2396-2402; Erices et al. (2000) Br. J. Haematol. 109:235-242 and Hou et al. (2003) Int. J. Hematol. 78:256-261. Additional sources of MSCs include, for example, adipose tissue, dental pulp and Wharton's jelly.

"Neuropoiesis" or "neuropoietic" refers or relates to the growth and/or differentiation of neural precursor cells (NPCs) into neurons and/or glial cells (e.g., astrocytes, oligodendrocytes). Examples of neuropoietic processes include, but are not limited to, NPC proliferation, neurogenesis (e.g., formation of new neurons) and gliogenesis (e.g., formation of astrocytes and/or oligodendrocytes). Other processes related to neuronal development include, for example, neurite outgrowth, outgrowth of axon(s), and outgrowth of dendrite(s).

The "Notch protein" (e.g., Notch 1 protein) is a transmembrane receptor, found in all metazoans, that influences cell differentiation through intracellular signaling. Contact of the Notch extracellular domain (e.g., the extracellular domain of the Notch 1 protein) with a Notch ligand (e.g., Delta, Serrate, Jagged) results in two proteolytic cleavages of the Notch protein, the second of which is catalyzed by a γ-secretase and releases the Notch intracellular domain (NICD) into the cytoplasm. In the mouse Notch protein, this cleavage occurs between amino acids gly1743 and val1744. The NICD translocates to the nucleus, where it acts as a transcription factor, recruiting additional transcriptional regulatory proteins (e.g., MAM, histone acetylases) to relieve transcriptional repression of various target genes (e.g., Hes 1). Additional details and information regarding Notch signaling are found, for example in Artavanis-Tsakonas et al. (1995) Science 268:225-232; Mumm and Kopan (2000) Develop. Biol. 228:151-165 and Ehebauer et al. (2006) Sci. STKE 2006 (364), cm7. [DOI: 10.1126/stke.3642006 cm7].

"Stroke" is the name given to conditions resulting from impairment of blood flow in the brain. Such cerebrovascular impairment can result, for example, from intracranial hemorrhage, or from reduction or blockage of blood flow in the brain (i.e., cerebral ischemia). Ischemic blockages can result from thrombosis (i.e., formation of a clot in situ in a cranial vessel or a vessel supplying the brain) or from a cerebral embolism migration of a clot to a site in the brain). The damage resulting from ischemic or hemorrhagic stroke usually results in impairment of certain neurological and physiological functions. Additional information relating to different types of stroke, and their characteristics, is found in co-owned U.S. Pat. Nos. 8,092,792 and 10,245,286; the disclosures of which are incorporated by reference in their entireties herein for the purpose of describing different types of stroke and their characteristics.

Treatments

FIG. 1 illustrates a method 100 of treating a subject with a stroke-induced motor deficit. The stroke-induced motor deficit can be the result of an ischemic stroke suffered by the subject. The method 100 can also be considered a method of treating a subject following an ischemic stroke or a method of treating a subject following a small-volume ischemic stroke.

The method 100 can comprise determining a volume of an ischemic core of the subject with the stroke-induced motor deficit in operation 102. In some instances, operation 102 can comprise receiving data or information concerning the volume of the ischemic core of the subject.

For purposes of the present disclosure, the ischemic core or infarct core can refer to brain tissue that has already infarcted (i.e., suffered necrosis or tissue death) or is irreversibly destined to infarct as a result of the ischemic stroke suffered by the subject.

The volume of the ischemic core can be determined using computed tomography (CT) perfusion (CTP), diffusion-weighted magnetic resonance imaging (DWI), or, on some occasions, baseline non-contrast CT (NCCT). When measured using CTP, the ischemic core can be defined as brain tissue with a relative cerebral blood flow (CBF) level of less than 30% of normal brain blood flow. When measured using DWI, the ischemic core can be defined as brain tissue with an apparent diffusion coefficient of less than 620 $\mu m^2/s$ [11].

In some instances, the method 100 can comprise proceeding with the cell therapy or treatment only when the ischemic core is determined to be less than 50 cubic centimeters (cc). For example, the method 100 can comprise only proceeding with the cell therapy or treatment when the ischemic core is determined to be between about 2 cc and 50 cc.

The method 100 can further comprise determining a degree of disability of the subject by determining an mRS score of the subject in operation 104. In some instances, operation 104 can comprise receiving data or information concerning the mRS score of the subject.

Although FIG. 1 illustrates operation 104 as following operation 102, it should be understood by one of ordinary skill in the art that the order of such operations can be switched or the operations can occur concurrently.

In some instances, the method 100 can comprise proceeding with the cell therapy or treatment only when the mRS score of the subject is between 2 and 4. For example, those with an mRS score of less than 2 can be considered not sufficiently disabled enough to warrant the cell therapy disclosed herein and those with an mRS score of greater than 4 can be considered too severely disabled for the treatment.

The method 100 can further comprise administering, to a brain region surrounding the ischemic core of the subject, a therapeutically effective amount of cells in operation 106. In some instances, the brain region surrounding the ischemic core can be an ischemic penumbra of the subject. The method 100 can comprise administering a therapeutically effective amount of cells to the ischemic penumbra without injecting directly into the ischemic core.

For purposes of the present disclosure, the ischemic penumbra can refer to hypo-perfused brain tissue or brain tissue which is at risk for irreversible damage but is still salvageable. Some studies have defined the ischemic penumbra as a region of reduced CBF where CBF levels are reduced to between approximately 10 and 15 ml/100 g/min and approximately 25 mL/100 g/min [12].

The method 100 can comprise administering, to the ischemic penumbra of the subject, a therapeutically effective amount of cells in operation 106. In some instances, the method 100 can comprise administering, to the ischemic penumbra of the subject, the therapeutically effective amount of cells only when the volume of the ischemic core is determined to be less than 50 cc. For example, the method 100 can comprise administering, to the ischemic penumbra of the subject, the therapeutically effective amount of cells only when the volume of the ischemic core is determined to be between about 2 cc and 50 cc.

In these and other instances, the method 100 can comprise administering, to the ischemic penumbra of the subject, the therapeutically effective amount of cells only when the mRS score of the subject is between 2 and 4. The method 100 can also comprise administering, to the ischemic penumbra of the subject, the therapeutically effective amount of cells only when the volume of the ischemic core is determined to be less than 50 cc and the mRS score of the subject is between 2 and 4.

As will be discussed in more detail in the following sections, the Applicant discovered that in subjects with an mRS score of between 2 and 4 who had suffered a small-volume stroke (e.g., ischemic core volume <50 cc), a statistically significant difference (p-value=0.02) was observed in the proportion of such subjects in the treatment group (i.e., those who were administered the cells) that exhibited clinically important improvements in their motor functioning than those same subjects in the sham/control group.

In certain instances, the method 100 can be considered a method of treating a subject with a chronic stroke-induced motor deficit or a method of treating chronic stroke. For example, the method 100 can comprise administering, to the brain region surrounding the ischemic core of the subject, the therapeutically effective amount of cells only when the ischemic stroke occurred more than six months prior (e.g., between six months and 90 months prior) to administering the cells.

The method 100 can also be considered a method of treating small-volume chronic stroke (as opposed to acute stroke). For example, the method 100 can comprise administering, to the brain region surrounding the ischemic core of the subject, the therapeutically effective amount of cells only when the ischemic stroke occurred more than six months prior (e.g., between six months and 90 months prior) to administering the cells and only when the volume of the ischemic core is determined to be less than 50 cc.

When the stroke incident occurred more than six months prior to treatment (e.g., administering the cells), the penumbra surrounding the chronic ischemic core of the subject can be considered a chronic penumbra (as opposed to an acute penumbra). The chronic penumbra can exhibit CBF levels even less than those exhibited by the acute penumbra of subjects who had recently suffered a stroke. In these instances, the method 100 of treating such patients can comprise administering, to the chronic penumbra surrounding the chronic ischemic core of the subject, the therapeutically effective amount of cells. In some instances, the method 100 can comprise administering, to the chronic penumbra surrounding the chronic ischemic core of the subject, the therapeutically effective amount of cells only when the volume of the chronic ischemic core is determined to be less than 50 cc.

DNTT-MSCs

The cells administered can be allogeneic cells descended from mesenchymal stem cells transiently-transfected by a polynucleotide encoding a Notch intracellular domain (NICD). The cells can be made by a method comprising providing a culture of the mesenchymal stem cells, contacting the culture of mesenchymal stem cells with the polynucleotide encoding a NICD (where the polynucleotide does not encode a full-length Notch protein), selecting cells that comprise the polynucleotide, and further culturing the selected cells in the absence of selection for the polynucleotide. The mesenchymal stem cells can be human bone marrow-derived cells. For purposes of this disclosure, the cells administered can be referred to as DNTT-MSCs.

As previously discussed, DNTT-MSCs can be obtained from marrow adherent stromal cells, also known as MSCs, by transiently expressing the intracellular domain of the Notch protein in the MSCs. Transient expression of the Notch intracellular domain (e.g., the NICD from the human Notch 1 protein)) in a MSC can be sufficient to convert a population of MSCs into a population of DNTT-MSCs. Additional treatment with growth and/or differentiation factors is not required. Thus, a population of MSCs can be converted to a population of DNTT-MSCs by transient transfection of MSCs with a vector comprising sequences encoding a NICD (but not encoding full-length Notch protein), followed by selection for cells comprising the vector and further culture of the selected cells in serum-containing medium, in the absence of exposure to additional growth and/or differentiation factors. See, for example, U.S. Pat. No. 7,682,825 (Mar. 23, 2010); U.S. Patent Application Publication No. 2010/0266554 (Oct. 21, 2010); and WO 2009/023251 (Feb. 19, 2009); the disclosures of which are incorporated herein by reference in their entireties for the purposes of describing isolation of mesenchymal stem cells and conversion of mesenchymal stem cells to DNTT-MSCs (denoted "neural precursor cells" and "neural regenerating cells" in those documents).

In these methods, any polynucleotide encoding a Notch intracellular domain (e.g., vector) can be used, and any method for the selection and enrichment of transfected cells can be used. For example, MSCs can be transfected with a vector containing sequences encoding a Notch intracellular domain (e.g., the human Notch 1 intracellular domain) and also containing sequences encoding a selection marker (e.g., drug resistance; e.g., resistance to G418). In some instances, two vectors, one containing sequences encoding a Notch intracellular domain and the other containing sequences encoding a drug resistance marker, can be used for transfection of MSCs. In these instances, selection is achieved, after transfection of a cell culture with the vector or vectors, by adding a selective agent (e.g., G418) to the cell culture in an amount sufficient to kill cells that do not comprise the vector but spare cells that do. Absence of selection entails removal of said selective agent or reduction of its concentration to a level that does not kill cells that do not comprise the vector. Following selection (e.g., for seven days) the selective agent can be removed and the cells can be further cultured (e.g., for two passages) in serum-containing culture medium.

It is also possible, depending on the nature of the selection marker and/or the concentration of the selective agent used, that not every cell that lacks a vector encoding a selection marker will be killed during the selection process. For example, a selective agent may inhibit growth of a cell not comprising the selection marker and, after removal of the selective agent, that cell may recover and resume growth.

Preparation of DNTT-MSCs thus involves transient expression of an exogenous Notch intracellular domain in a MSC. To this end, MSCs can be transfected with a vector comprising sequences encoding a Notch intracellular domain (e.g., the human Notch 1 intracellular domain) wherein said sequences do not encode a full-length Notch protein. All such sequences are known and readily available to those of skill in the art. For example, Del Amo et al. (1993) Genomics 15:259-264 present the complete amino acid sequences of the mouse Notch protein; while Mumm and Kopan (2000) Devel. Biol. 228:151-165 provide the amino acid sequence, from mouse Notch protein, surrounding the so-called S3 cleavage site which releases the intracellular domain. Taken together, these references provide the skilled artisan with each and every peptide containing a Notch intracellular domain that is not the full-length Notch protein; thereby also providing the skilled artisan with every polynucleotide comprising sequences encoding a Notch intracellular domain that does not encode a full-length Notch protein. The foregoing documents (Del Amo and Mumm) are incorporated by reference in their entireties for the purpose of disclosing the amino acid sequence of the full-length Notch protein and the amino acid sequence of the Notch intracellular domain, respectively.

Similar information is available for Notch proteins and nucleic acids from additional species, including rat, *Xenopus*, *Drosophila* and human. See, for example, Weinmaster et al. (1991) Development 113:199-205; Schroeter et al. (1998) Nature 393:382-386; NCBI Reference Sequence No. NM_017167 (and references cited therein); SwissProt P46531 (and references cited therein); SwissProt Q01705 (and references cited therein); and GenBank CAB40733 (and references cited therein). The foregoing references are incorporated by reference in their entireties for the purpose of disclosing the amino acid sequence of the full-length Notch protein and the amino acid sequence of the Notch intracellular domain in a number of different species.

In some instances, DNTT-MSCs can be prepared by introducing, into MSCs, a nucleic acid comprising sequences encoding a Notch intracellular domain such that the MSCs do not express exogenous Notch extracellular domain. Such can be accomplished, for example, by transfecting MSCs with a vector comprising sequences encoding a Notch intracellular domain wherein said sequences do not encode a full-length Notch protein.

Additional details on the preparation of DNTT-MSCs, and methods for making cells with properties similar to those of DNTT-MSCs which can be used in the methods disclosed herein, can be found in U.S. Pat. No. 7,682,825 (Mar. 23, 2010); and U.S. Patent Application Publication Nos. 2010/0266554 (Oct. 21, 2010) and 2011/0229442 (Sep. 22, 2011); the disclosures of which are incorporated herein by reference in their entireties for the purposes of describing alternative methods for the preparation of, DNTT-MSCs, and for providing methods for making cells with properties similar to those of DNTT-MSCs. See also Dezawa et al. (2004) J. Clin. Invest. 113:1701-1710.

Cell Culture

Standard methods for cell culture are known in the art. See, for example, R. I. Freshney "Culture of Animal Cells: A Manual of Basic Technique," Fifth Edition, Wiley, New York, 2005.

Transfection

Methods for introduction of exogenous DNA into cells (i.e., transfection), and selection of transfected cells, are also known in the art. See, for example, Sambrook et al. "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates.

Figure 2:
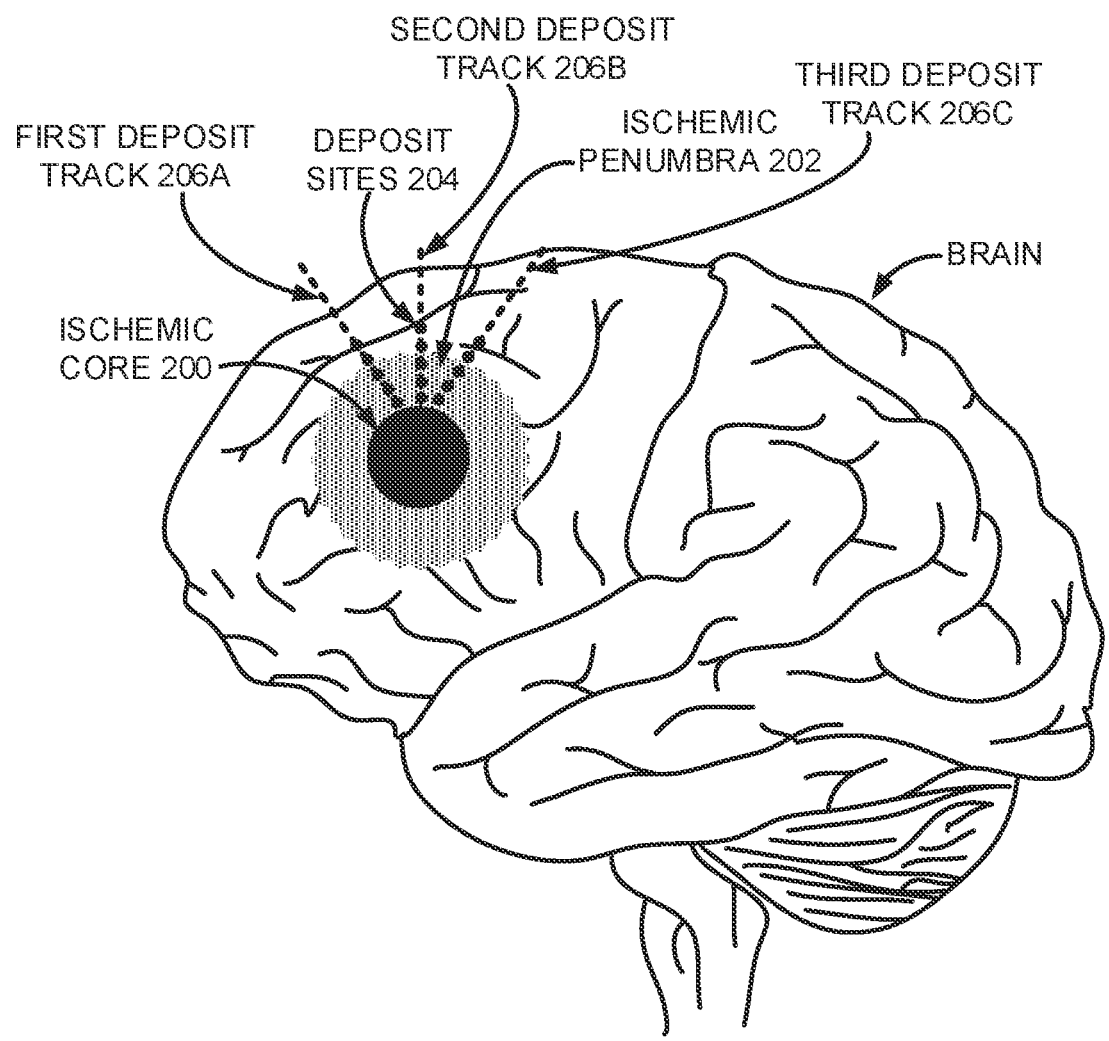
FIG. 2 illustrates an ischemic core of a stroke patient surrounded by an ischemic penumbra.

FIG. 2 depicts an ischemic core 200 of a subject having suffered an ischemic stroke. As shown in FIG. 2, the ischemic core 200 can be surrounded by an ischemic penumbra 202. When the ischemic stroke occurred more than six-months prior to the commencement of treatment, the ischemic core 200 can be considered a chronic ischemic core and the ischemic penumbra 202 can be considered a chronic ischemic penumbra.

As previously discussed, the ischemic core 200 can have a core volume or ischemic core volume. The core volume can be determined using, among other imaging techniques, computed tomography perfusion or diffusion-weighted magnetic resonance imaging. When the core volume is determined to be less than 50 cc (for example, between about 2 cc and 50 cc), the ischemic stroke can be considered a small-volume ischemic stroke.

Also, as previously discussed, a method of treating a small-volume ischemic stroke can comprise administering a therapeutically effective amount of allogeneic cells to an ischemic penumbra surrounding a small-volume ischemic core 200 of a subject having suffered the small-volume ischemic stroke. The cells can be descended from mesenchymal stem cells transiently-transfected by a polynucleotide encoding a NICD. For purposes of this disclosure, the cells can be referred to as DNTT-MSCs. Moreover, when the ischemic stroke occurred more than six-months prior to the commencement of the treatment, the method can be considered a method of treating a small-volume chronic ischemic stroke.

As shown in FIG. 2, the method can comprise administering the therapeutically effective amount of the cells by injecting a cell suspension comprising the cells at one or more deposit sites 204 within the brain of the subject. The step of administering the therapeutically effective amount of the cells can further comprise injecting at least part of the cell suspension comprising the cells at one or more deposit sites 204 at an outer periphery of the ischemic penumbra or chronic ischemic penumbra surrounding the small-volume ischemic core. For example, the step of administering the therapeutically effective amount of the cells can comprise injecting at least part of the cell suspension comprising the cells at one or more deposit sites 204 proximal to the ischemic penumbra or chronic ischemic penumbra surrounding the small-volume ischemic core.

The step of administering the therapeutically effective amount of the cells can also comprise injecting at least part of the cell suspension comprising the cells at one or more deposit sites 204 within the ischemic penumbra surrounding the small-volume ischemic core. In some instances, the step of administering the therapeutically effective amount of the cells can comprise injecting at least part of the cell suspension comprising the cells at one or more deposit sites 204 distal to the ischemic penumbra or the ischemic chronic penumbra. In these and other instances, the step of administering the therapeutically effective amount of the cells can comprise injecting at least part of the cell suspension comprising the cells at one or more deposit sites 204 within the small-volume ischemic core.

The cell suspension can comprise the cells suspended in a pharmaceutically acceptable carrier or diluent. In some instances, the pharmaceutically acceptable carrier or diluent can be a sterile isotonic crystalloid solution. For example, the cell suspension can comprise the cells suspended in Plasma-Lyte™ A (Baxter Healthcare Corporation). The cells can also be suspended in another physiologically compatible carrier such as phosphate buffered saline.

The cells can be administered stereotactically via a single burr-hole craniostomy. Additional details on stereotactic administration of the cells can be found in U.S. Patent Publication No. US 2019/0290846 (Sep. 26, 2019), the content of which is incorporated herein by reference in its entirety for the purposes of describing stereotactic administration of DNTT-MSCs and equipment used for such purposes.

The method can further comprise subjecting a formulated dose of the cells to post-release testing prior to administering the cells to the subject.

The therapeutically effective amount of cells (or DNTT-MSCs) can be approximately 2.5 million cells (or 2.5 million cells±0.1 million cells). When the amount of cells administered is approximately 2.5 million cells, the treatment method can comprise injecting a cell suspension comprising the cells at five deposit sites 204 (see FIG. 2) along a first deposit track 206A or needle track, five deposit sites 204 along a second deposit track 206B or needle track, and five deposit sites along a third deposit track 206C or needle track. Approximately 20-μL of the cell suspension can be injected at each deposit site. Moreover, the cell suspension can have a cell concentration of approximately $8.5*10^6$ cells/mL.

The therapeutically effective amount of cells (or DNTT-MSCs) can be approximately 5.0 million cells (or 5.0 million cells±0.1 million cells). When the amount of cells administered is approximately 5.0 million cells, the treatment method can comprise injecting a cell suspension comprising the cells at five deposit sites 204 (see FIG. 2) along a first deposit track 206A or needle track, five deposit sites 204 along a second deposit track 206B or needle track, and five deposit sites along a third deposit track 206C or needle track. Approximately 20-μL of the cell suspension can be injected at each deposit site. Moreover, the cell suspension can have a cell concentration of approximately $17.0*10^6$ cells/mL.

In some cases, the therapeutically effective amount of cells (or DNTT-MSCs) can be between approximately 2.5 million cells and 5.0 million cells. For example, the therapeutically effective amount of cells (or DNTT-MSCs) can be approximately 3.0 million cells (or 3.0 million cells±0.1 million cells), 3.5 million cells (or 3.5 million cells±0.1 million cells), 4.0 million cells (or 4.0 million cells±0.1 million cells), or 4.5 million cells (or 4.5 million cells±0.1 million cells).

As shown in FIG. 2, at least some of the deposit sites 204 along each of the deposit tracks or needle tracks can be within the ischemic penumbra or chronic ischemic penumbra. In some instances, at least one or more of the deposit sites 204 along each of the deposit tracks or needle tracks can be proximal to or at the outer periphery of the ischemic penumbra or chronic ischemic penumbra. In other instances, all of the deposit tracks or needle tracks can be within the ischemic penumbra or chronic ischemic penumbra. In additional instances, at least one or more of the deposit sites 204 along each of the deposit tracks or needle tracks can be within or at an outer periphery of the ischemic core or chronic ischemic core.

In certain instances, the treatment is especially effective when the ischemic core 200 is located in a region, lobe, or area of the brain of the subject other than a parietal region or lobe. For example, the method of treating the small-volume ischemic stroke can comprise administering, the therapeutically effective amount of cells, to the brain region (e.g., the ischemic penumbra 202) surrounding the ischemic core 200 of the subject only when part of the ischemic core 200 is located in at least one of a cortical frontal region, a cortical temporal region, a subcortical white matter, and a subcortical grey matter of the brain of the subject (see, e.g., FIG. 5). In some instances, the method can comprise administering, to the brain region (e.g., the ischemic penumbra 202) surrounding the ischemic core 200 of the subject, the therapeutically effective amount of cells only when the ischemic core 200 is located in a region of the brain of the subject other than a parietal region.

Composition, Formulations, and Kits

Also disclosed are compositions, formulations, and kits for treating small-volume ischemic stroke or small-volume chronic ischemic stroke. The composition can comprise a therapeutically effective amount of cells and a pharmaceutically acceptable carrier or diluent. As previously discussed, the cells, also referred to as DNTT-MSCs, can be descended from mesenchymal stem cells transiently-transfected by a polynucleotide encoding a Notch intracellular domain (NICD). The cells (DNTT-MSCs) can be made by a process comprising providing a culture of the mesenchymal stem cells (e.g., human bone marrow-derived cells) and contacting the culture of mesenchymal stem cells with the polynucleotide encoding the NICD. For example, the mesenchymal stem cells can be transiently-transfected with a plasmid comprising the polynucleotide encoding the NICD. The process can further comprise selecting cells that comprise the polynucleotide, and further culturing the selected cells in the absence of selection for the polynucleotide. In certain instances, the polynucleotide does not encode a full-length Notch protein. The compositions disclosed herein can be useful for, inter alia, stimulating proliferation and differentiation of neural precursor cells and/or endothelial cells.

The "therapeutically effective amount" of the composition can comprise cells of an amount suitable for treatment of small-volume ischemic stroke or small-volume chronic ischemic stroke by, inter alia, stimulating proliferation and differentiation of neural precursor cells and/or endothelial cells. In some instances, the therapeutically effective amount of the composition can comprise approximately 2.5 million cells (or 2.5 million cells±0.1 million cells). The therapeutically effective amount of the composition can also comprise approximately 5.0 million cells (or 5.0 million cells±0.1 million cells). The therapeutically effective amount of the composition can also comprise between approximately 2.0 million cells and approximately 5.0 million cells.

In other instances, the therapeutically effective amount of the composition can vary based on the nature and severity of the injury, the weight and general health of the subject and other criteria that are known to those of skill in the art. For example, dosage amounts can vary from about 100; 500; 1,000; 2,500; 5,000; 10,000; 20,000; 50,000; 100,000; 500,000; 1,000,000; 2,500,000; 5,000,000 to 10,000,000 cells or more (or any integral value therebetween); with a frequency of administration of, e.g., a single dose, once per day, twice per week, once per week, twice per month, once per month, depending upon, e.g., body weight, route of administration, severity of disease, etc.

The cells described herein can be suspended in a pharmaceutically acceptable carrier or diluent to form the cell suspension. The pharmaceutically acceptable carrier can be a physiologically compatible carrier for implantation. As used herein, the term "physiologically compatible carrier" can refer to a carrier that is compatible with the other ingredients of the formulation and not deleterious to the recipient thereof. Examples of suitable carriers or diluents include cell culture medium (e.g., Eagle's minimal essential medium), phosphate buffered saline, Hank's balanced salt solution+/−glucose (HBSS), and multiple electrolyte solutions. The pharmaceutically acceptable carrier or diluent can also be or comprise a sterile isotonic crystalloid solution such as Plasma-Lyte™ A (Baxter Healthcare Corporation).

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The composition can comprise the cell suspension packaged in a sealed vial. In some instances, the sealed vial can comprise 0.3 mL of the cell suspension with a cell concentration of approximately $8.5*10^6$ cells/mL. Alternatively, the sealed vial can comprise 0.3 mL of the cell suspension with a cell concentration of approximately $17.0*10^6$ cells/mL.

Also disclosed are other examples of materials which can serve as pharmaceutically-acceptable carriers including: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Exemplary formulations include, but are not limited to, those suitable for parenteral administration, e.g., intrapulmonary, intravenous, intra-arterial, intra-ocular, intra-cranial, sub-meningeal, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure can vary according to the extent and severity of the need for treatment, the activity of the administered composition, the general health of the subject, and other considerations well known to the skilled artisan.

In additional embodiments, the compositions described herein can also be delivered locally. Localized delivery allows for the delivery of the composition non-systemically, thereby reducing the body burden of the composition as compared to systemic delivery. Such local delivery can be achieved, for example, through the use of various medically implanted devices including, but not limited to, stents and catheters, or can be achieved by inhalation, injection or surgery. Methods for coating, implanting, embedding, and otherwise attaching desired agents to medical devices such as stents and catheters are established in the art and contemplated herein.

Another aspect of the present disclosure relates to kits for carrying out the administration of the cells to a subject. For example, the kit can comprise the composition of cells, formulated as appropriate (e.g., in a pharmaceutical carrier), in one or more separate pharmaceutical preparations.

Compositions comprising DNTT-MSCs can be used in combination with other compositions comprising substances that stimulate angiogenesis ("pro-angiogenic agents"). The compositions can be administered sequentially in any order or concurrently. Accordingly, therapeutic compositions as disclosed herein can contain both DNTT-MSCs and a pro-angiogenic agent. In additional embodiments, separate therapeutic compositions, one comprising DNTT-MSCs and the other comprising a pro-angiogenic agent, can be administered to the subject, either separately or together.

In some instances, the pro-angiogenic agent can be a protein (e.g., fibroblast growth factor, platelet-derived growth factor, transforming growth factor alpha, hepatocyte growth factor, vascular endothelial growth factor, sonic hedgehog, MAGP-2, HIF-1, PR-39, RTEF-1, c-Myc, TFII, Egr-1, ETS-1) or a nucleic acid encoding such a protein. See, for example, Vincent et al. (2007) Gene Therapy 14:781-789. In other instances, the pro-angiogenic agent can be a small RNA molecule (e.g., siRNA, shRNA, microRNA) or a ribozyme that targets a nucleic acid encoding an inhibitor of angiogenesis. Moreover, the pro-angiogenic agent can be a triplex-forming nucleic acid that binds to DNA sequences regulating the expression of a protein that inhibits angiogenesis, such as to block transcription of the gene encoding the protein.

The pro-angiogenic agent can be a transcription factor that activates expression of a pro-angiogenic molecule (e.g., protein). Naturally-occurring transcription factors (such as, for example, HIF-1alpha) that regulate the expression of pro-angiogenic proteins, are known. In addition, synthetic transcriptional regulatory proteins can be constructed by genetic engineering. For example, methods for the design of zinc finger DNA-binding domains that bind to a sequence of interest, and methods for the fusion of such zinc finger DNA-binding domains to transcriptional activation and repression domains, have been described. See, for example, U.S. Pat. Nos. 6,534,261: 6,607,882; 6,785,613; 6,794,136; 6,824,978; 6,933,1 6,979,539; 7,013,219: 7,177,766; 7,220,719; and 7,788,044. These methods can be used to synthesize non-naturally-occurring proteins that activate transcription of any gene encoding a pro-angiogenic protein. In addition, synthetic zinc finger transcriptional activators of the vascular endothelial growth factor (VEGF) gene have been described. See, e.g., U.S. Pat. Nos. 7,026,462; 7,067, 317; 7,560,440: 7,605,140; and 8,071,564. Accordingly, a non-naturally-occurring (i.e., synthetic) zinc finger protein that activates transcription of the VEGF gene can be used, in combination with SB623 cells, for augmenting angiogenesis, e.g., in the treatment of stroke. Furthermore, a natural or synthetic transcriptional regulatory protein (e.g., a synthetic zinc finger transcriptional regulatory protein) that inhibits transcription of an anti-angiogenic molecule can also be used as a pro-angiogenic agent.

Clinical Trial

A randomized double-blind sham surgery-controlled clinical trial was conducted evaluating the safety and efficacy of stereotactic intracranial injection of DNTT-MSCs (also known as SB623 cells) in subjects suffering from chronic motor deficits as a result of ischemic stroke. The subjects were randomized as part of the clinical trial at a ratio of roughly 1:1:1 to receive: (1) approximately 2.5 million DNTT-MSCs, (2) approximately 5.0 million DNTT-MSCs, or (3) the sham surgery (the control group). A total of 158 subjects were randomized with 51 subjects receiving the sham surgery, 52 subjects receiving the approximately 2.5 million DNTT-MSCs, and 55 subjects receiving the approximately 5.0 million DNTT-MSCs.

Study Population and Administration Procedure

The study population included adult subjects with chronic motor deficits caused by an ischemic stroke event occurring between 6 months and 90 months (7.5 years) prior. The post-stroke interval of 6 months to 90 months was selected based on studies that had shown that more than 90% of ischemic stroke subjects were stable by 90 days post-stroke. All subjects also had an mRS score of between 2 and 4 at screening. Subjects with an mRS score of less than 2 were deemed not sufficiently disabled to justify the risk of such a procedure and subjects with an MRS score of greater than 4 were considered at increased risk due to severe disability).

As previously discussed, a total of 158 subjects were randomized as part of the clinical trial with 51 subjects receiving the sham surgery and 107 subjects receiving the treatment (either the approximately 2.5 million or the approximately 5.0 million DNTT-MSCs). Of the 158 subjects, 77 subjects had suffered a small-volume ischemic stroke or a stroke with an ischemic core volume of less than 50 cc (based on CT or MRI scans included as part of the subjects' medical history).

The subjects received either the sham surgery or an intracranial administration of approximately 2.5 million DNTT-MSCs or approximately 5.0 million DNTT-MSCs. The DNTT-MSCs were administered stereotactically through a single burr-hole craniostomy.

The one burr-hole craniostomy (about 1 cm to about 1.5 cm) was fashioned under local anesthesia and sedation. The subject's dura was opened and an implantation cannula was inserted. Five 20-µL volumes of a cell suspension comprising the DNTT-MSCs were injected slowly into five implantation sites selected by stereotactic targeting (so a total of 100-μL of the cell suspension was injected among the five implantation sites along a single deposit track). This procedure was repeated with two other deposit tracks with different trajectories inserted through the same burr-hole craniostomy (see, e.g., FIG. 2). Those who received the approximately 2.5 million DNTT-MSCs were injected with a cell suspension having a target concentration of approximately $8.5*10^6$ cells/mL and those who received the approximately 5.0 million DNTT-MSCs were injected with a cell suspension having a target concentration of approximately $17*10^6$ cells/mL.

The sham surgical group received a sham surgery under local anesthesia and sedation with the same stereotactic planning procedure, partial-thickness skull outer table burr hole, and scalp sutures but no penetration of the dura matter or cell implantation. The sham surgery procedure was scripted to mimic as closely as possible the procedure undertaken by the treatment group.

The DNTT-MSCs or SB623 cells were provided as sterile cell suspensions in a unit volume of 1 mL containing $≥8*10^6$ cells/mL and cryopreserved in CryoStore™ freezing media in a 2 mL vial. The cryopreserved cells were thawed, washed, centrifuged, and re-suspended in Plasma-Lyte A to achieve the aforementioned target concentrations. Prior to administration, the formulated dose for injection underwent post release testing and the formulated dose for injection was administered to the subject within three hours post-release testing.

Results of Clinical Trial

With respect to safety, DNTT-MSCs administered to subjects intracranially at doses of approximately 2.5 million cells or approximately 5.0 million cells were well tolerated in all subjects with stroke-induced chronic motor deficits.

With respect to efficacy, the study did not meet its primary efficacy endpoint of a statistically significant difference in the proportion of subjects in the "combined treatment group" (those who were administered either the ~2.5 million cells or the ~5.0 million cells) that exhibited an improvement of at least 10-points in their total FMMS over the control/sham group at week 24 (~month 6). The response rate was similar in the sham surgery group (~15.6%) and the combined treatment group (~15.0%) and there was no statistically significant difference between the combined treatment group response rate and the sham surgery response rate based on statistical analysis using generalized linear mixed model (GLMM) analysis or logistic regression analysis.

Retrospective Analysis of Clinical Trial Data

A retrospective analysis was conducted of data collected from the aforementioned clinical trial.

With respect to efficacy, one unexpected result discovered by the Applicant from the retrospective analysis was that in subjects who had suffered a small-volume stroke (e.g., ischemic core volume <50 cc), a statistically significant difference (p-value=0.02) was observed in the proportion of subjects in the combined treatment group (i.e., those who were administered either the ~2.5 million cells or the ~5.0 million cells) that exhibited clinically important improvements in their motor functioning compared to the sham/control group. In view of these unexpected findings, administration of DNTT-MSCs may be considered an effective treatment for subjects suffering from chronic motor deficits caused by a small-volume ischemic stroke.

In addition, another unexpected result discovered by the Applicant was that in subjects who had suffered a stroke in a region/lobe of the brain not in the parietal region/lobe (i.e., the ischemic of the stroke was located in a region/lobe of the brain not in the parietal region/lobe), a statistically significant difference (p-value=0.05) was observed in the proportion of subjects in the combined treatment group that exhibited clinically important improvements in their motor functioning compared to the sham/control group.

Moreover, yet another unexpected result discovered by the Applicant was that in subjects who had suffered a small-volume stroke (e.g., ischemic core volume <50 cc) in a region of the brain not in the parietal region/lobe, an even greater statistically significant difference (p-value <0.01) was observed in the proportion of subjects in the combined treatment group that exhibited clinically important improvements in their motor functioning compared to the sham/control group.

As part of the retrospective analysis, clinical trial subjects were considered "Composite Responders" if they exhibited clinically meaningful improvements in their motor functioning by achieving at least one of the following MCID thresholds (the "MCID Thresholds"):

1. Change from baseline ("CFB") improvement in their total FMMS at week 24 ("W24") of at least 9 points (W24 CFB Total FMMS Improvement ≥9 points)
2. CFB improvement in their total FMMS UE at week 24 of at least 6 points (W24 CFB FMMS UE Improvement ≥6 points)
3. CFB improvement in their total FMMS LE at week 24 of at least 4 points (W24 CFB FMMS LE Improvement ≥4 points)

Tables 1 and 2 below show the composite response rates, average baseline scores, and average stroke volumes for the overall population and the small-volume stroke subpopulation, respectively.

TABLE 1

Treatment and control group values at 24 weeks for overall population

| Group | Count | Composite Responders | Response Rate | Average Baseline FMMS | Average Baseline mRS | Average Volume of Stroke |
|---|---|---|---|---|---|---|
| Combined Treatment Group | 107 | 42 | 39% | 44.87 | 2.74 | 53.19 |
| Control Group | 51 | 16 | 31% | 47.35 | 2.49 | 56.32 |

TABLE 2

Treatment and control group values at 24 weeks for small-volume stroke (ischemic core volume < 50 cc) population

| Group | Count | Composite Responders | Response Rate | Average Baseline FMMS | Average Baseline mRS | Average Volume of Stroke |
|---|---|---|---|---|---|---|
| Combined Treatment Group | 51 | 25 | 49% | 48.55 | 2.69 | 15.26 |
| Control Group | 26 | 5 | 19% | 49.42 | 2.54 | 14.4 |

Table 3 below shows the delta composite response rates and their accompanying p-values for the overall population and the small-volume stroke subpopulation. For purposes of this disclosure, a "delta composite response rate" refers to a difference in response rates between the treatment group and the control group.

TABLE 3

Delta composite response values and accompanying p-values for overall population and small-volume stroke population at 24 weeks

| Group | Treatment Count | Treatment Composite Responders | Control Count | Control Composite Responders | Delta Composite Response Rate | p-value of Delta Composite Response Rate |
|---|---|---|---|---|---|---|
| Overall Population | 107 | 42 | 51 | 16 | 8% | 0.42 |
| Small-Volume Stroke Population | 51 | 25 | 26 | 5 | 30% | 0.02 |

As shown by Tables 1-3 above, the population subsegment with small-volume stroke (e.g., patients who suffered an ischemic stroke with an ischemic core volume <50 cc) had a significantly higher response rate (~49%) in the treatment arm in comparison to the control arm (~19%). The delta composite response rate of ~30% for this population subsegment was determined to be statistically significant (p-value=0.02) based on GLMM and logistic regression analysis. This is in stark contrast to the delta composite response rate of 8% for the overall population, which was determined to be not statistically significant (p-value=0.42).

The retrospective analysis also determined that this statistically significant delta composite response rate is driven by the subjects' volume of stroke rather than the subjects' baseline mRS. More specifically, the subjects' volume of stroke did not have any considerable effect (and did not materially impact) the subjects' baseline mRS.

Figure 3A:
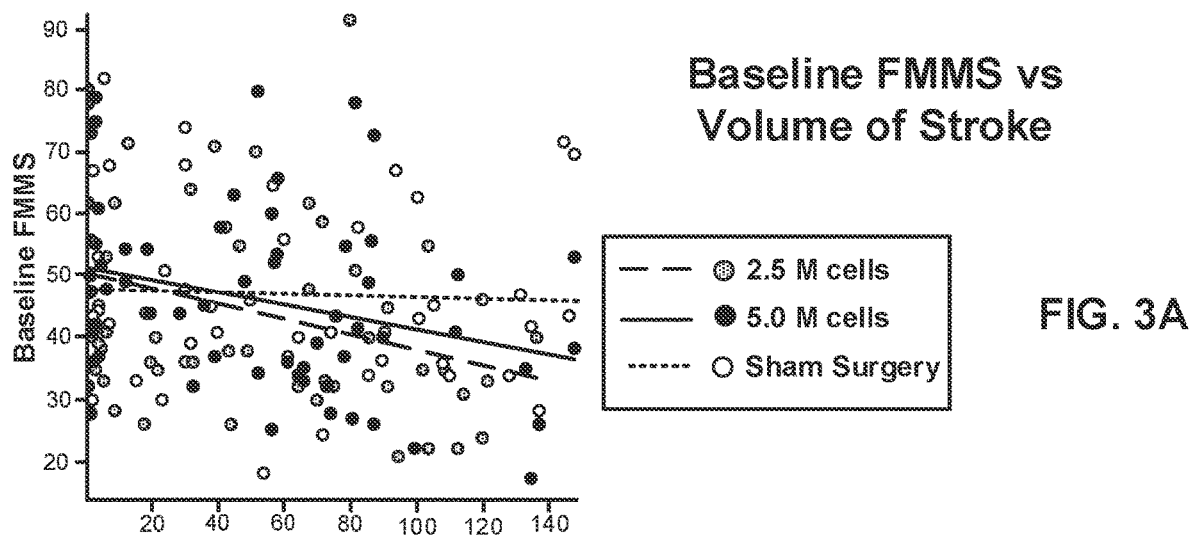
FIG. 3A illustrates the relationship between baseline FMMS and volume of stroke for various treatment and control groups.
Figure 3B:
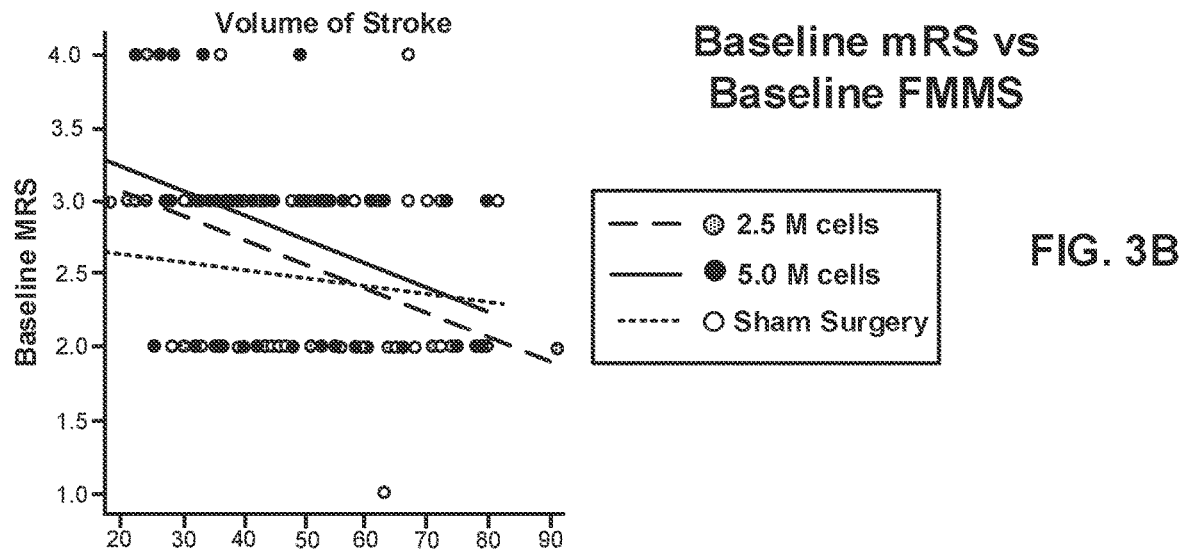
FIG. 3B illustrates the relationship between baseline mRS and baseline FMMS for various treatment and control groups.
Figure 3C:
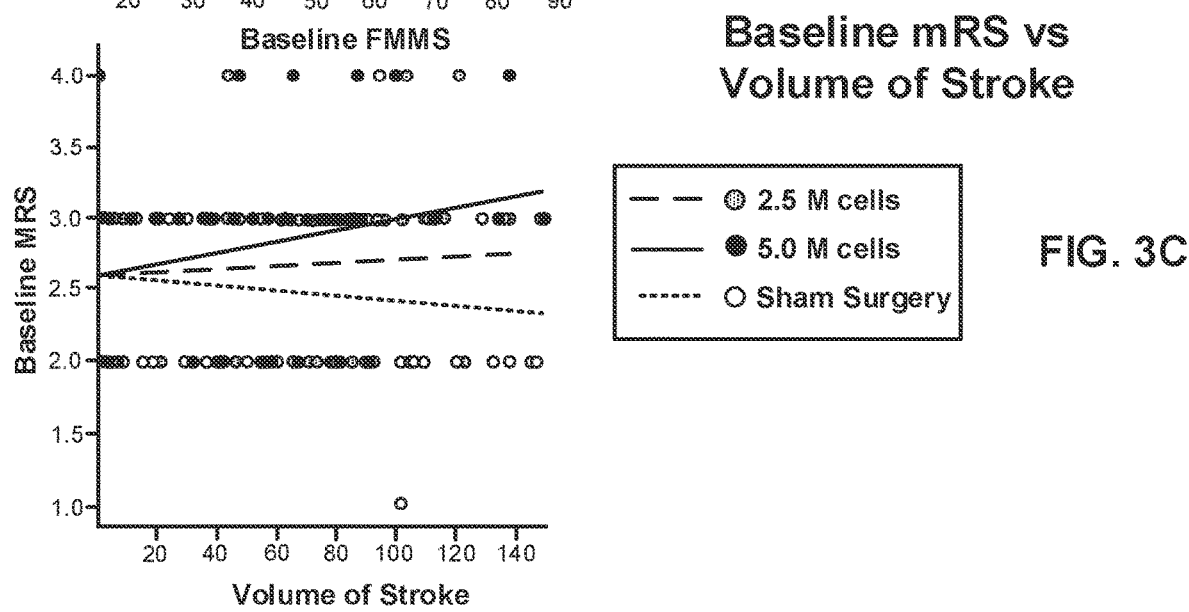
FIG. 3C illustrates the relationship between baseline mRS and volume of stroke for various treatment and control groups.

FIGS. 3A-3C are plots illustrating the relationship between baseline FMMS, baseline mRS, and volume of stroke (e.g., the volume of the stroke patients' ischemic core) for the 2.5 million (2.5 M) dosage group, the 5.0 million (5.0 M) dosage group, and the control group. FIG. 3A illustrates the relationship between baseline FMMS and volume of stroke for the 2.5 M dosage group, the 5.0 M dosage group, and the control group. A Spearman correlation was calculated between these two factors yielding a correlation of −0.23 with a p-value of 0.002. This indicates that the subjects' baseline FMMS is significantly correlated with the subjects' volume of stroke meaning that those with smaller stroke volumes generally exhibited greater motor function than those with larger stroke volumes.

FIG. 3B illustrates the relationship between baseline mRS and baseline FMMS for the 2.5 M dosage group, the 5.0 M dosage group, and the control group. A Spearman correlation was calculated between these two factors yielding a correlation of −0.34 with a p-value of <0.001. This indicates that the subjects' baseline mRS is significantly correlated with the subjects' baseline FMMS meaning that those subjects with less baseline motor function generally were more disabled than subjects with greater baseline motor function.

FIG. 3C illustrates the relationship between baseline mRS and volume of stroke for the 2.5 M dosage group, the 5.0 M dosage group, and the control group. A Spearman correlation was calculated between these two factors yielding a correlation of 0.06 with a p-value of 0.44. This indicates that the subjects' baseline mRS is not significantly correlated with the subjects' volume of stroke.

Dosage Comparison

Table 4 below shows composite response rates, average baseline scores, and average stroke volumes of all subjects broken down by treatment dosage, the control population, and the overall population.

TABLE 4

Composite response rates, average baseline scores, and average stroke volumes for various populations at 24 weeks

| Population | Count | Composite Responders | Response Rate | Average Baseline FMMS | Average Baseline mRS | Average Volume of Stroke |
|---|---|---|---|---|---|---|
| 2.5M Cell Dose | 52 | 24 | 46.15% | 44.38 | 2.65 | 48.82 |
| 5.0M Cell Dose | 55 | 18 | 32.73% | 45.33 | 2.82 | 57.33 |
| Control | 51 | 16 | 31.37% | 47.35 | 2.49 | 56.32 |
| Overall (2.5M + 5.0M + Control) | 158 | 58 | 36.71% | 45.67 | 2.66 | 54.20 |

Table 5 below shows composite response rates, average baseline scores, and average stroke volumes of subjects with small-volume strokes (e.g., patients who suffered an ischemic stroke with an ischemic core volume <50 cc) broken down by treatment dosage, the control population, and the overall population.

TABLE 5

Composite response rates, average baseline scores, and average stroke volumes for various small-volume stroke populations at 24 weeks

| Population | Count | Composite Responders | Response Rate | Average Baseline EMMS | Average Baseline mRS | Average Volume of Stroke |
|---|---|---|---|---|---|---|
| 2.5M Cell Dose | 29 | 16 | 55.17% | 48.17 | 2.66 | 15.02 |
| 5.0M Cell Dose | 22 | 9 | 40.91% | 49.05 | 2.73 | 15.58 |
| Control | 26 | 5 | 19.23% | 49.42 | 2.54 | 14.40 |
| Overall (2.5M + 5.0M + Control) | 77 | 30 | 38.96% | 48.84 | 2.64 | 14.97 |

Table 6 below shows composite response rates, average baseline scores, and average stroke volumes of subjects with stroke volumes equal to or greater than 50 cc (e.g., patients who suffered an ischemic stroke with an ischemic core volume 50 cc) broken down by treatment dosage, the control population, and the overall population.

TABLE 6

Composite response rates, average baseline scores, and average stroke volumes for various stroke subject populations with stroke volumes equal to or greater than 50 cc at 24 weeks

| Population | Count | Composite Responders | Response Rate | Average Baseline FMMS | Average Baseline mRS | Average Volume of Stroke |
|---|---|---|---|---|---|---|
| 2.5M Cell Dose | 23 | 8 | 34.78% | 39.61 | 2.65 | 91.43 |
| 5.0M Cell Dose | 33 | 9 | 27.27% | 42.85 | 2.88 | 85.17 |
| Control | 25 | 11 | 44.00% | 45.20 | 2.44 | 99.91 |
| Overall (2.5M + 5.0M + Control) | 81 | 28 | 34.57% | 42.65 | 2.68 | 91.50 |

Table 7 below shows composite response rates, average baseline scores, and average stroke volumes of subjects with stroke volumes equal to or greater than 100 cc (e.g., patients who suffered an ischemic stroke with an ischemic core volume ≥100 cc) broken down by treatment dosage, the control population, and the overall population.

TABLE 7

Composite response rates, average baseline scores, and average stroke volumes for various stroke subject populations with stroke volumes equal to or greater than 100 cc at 24 weeks

| Population | Count | Composite Responders | Response Rate | Average Baseline FMMS | Average Baseline mRS | Average Volume of Stroke |
|---|---|---|---|---|---|---|
| 2.5M Cell Dose | 9 | 3 | 33.33% | 33.00 | 3.00 | 114.08 |
| 5.0M Cell Dose | 7 | 2 | 28.57% | 37.14 | 3.14 | 132.83 |
| Control | 13 | 5 | 38.46% | 46.46 | 2.23 | 124.82 |
| Overall (2.5M + 5.0M + Control) | 29 | 10 | 34.48% | 40.03 | 2.69 | 123.42 |

Tables 4-7 above shows that when treatment populations are subdivided by dosage (e.g., 2.5 M cell dosage or the 5.0 M cell dosage) and compared with the control population, those subjects who were administered approximately 2.5 million DNTT-MSCs responded better than those subjects who were administered approximately 5.0 million DNTT-MSCs. This was maintained across all stroke-volume subpopulations as shown in Tables 5-7.

Figure 4:
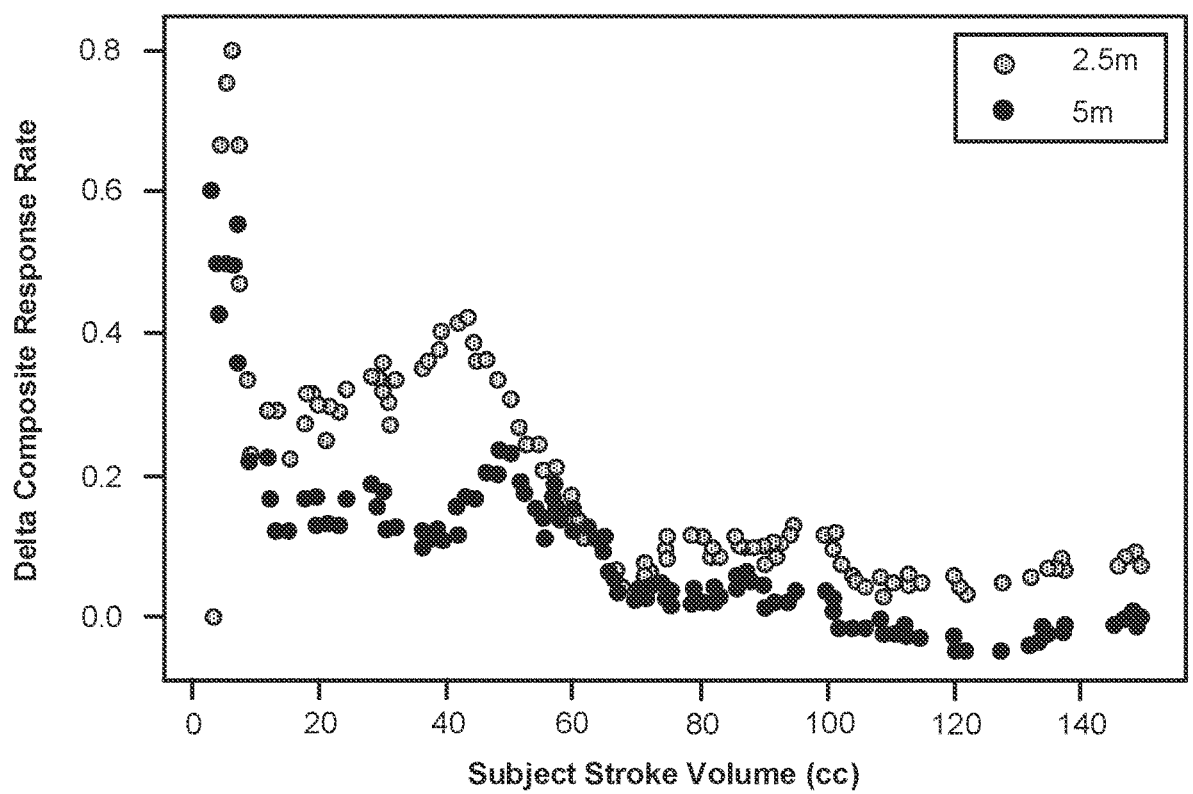
FIG. 4 illustrates the delta composite rate as a function of stroke volume for different dosage groups.

FIG. 4 illustrates that the delta composite response rate (or the difference in the composite response rate between the treatment group and the control group) for the 2.5 M dosage population exceeded the delta composite response rate for the 5.0 M dosage population across almost all subject stroke-volumes. As can be seen FIG. 4, the difference in the delta composite response rates is especially pronounced in subjects with small-volume strokes (e.g., patients who suffered an ischemic stroke with an ischemic core volume <50 cc). These results were unexpected and suggest that a dosage of 2.5 million DNTT-MSCs may be an even more therapeutically effective dose for treatment of chronic ischemic stroke than a dosage of 5.0 million DNTT-MSCs, despite the latter having more cells. This may be especially true for subjects with small-volume strokes (e.g., patients who suffered an ischemic stroke with an ischemic core volume <50 cc).

The graph in FIG. 4 excluded results for subjects with stroke-volumes below 2 cc (e.g., patients who suffered an ischemic stroke with an ischemic core volume <2 cc) as the number of subjects with stroke-volumes less than 2 cc in the control group greatly exceeded the number of such subjects in the 5.0 M dosage group from a relative standpoint.

Tables 5-7 also shows that with the exception of the small-volume stroke subpopulation (e.g., patients who suffered an ischemic stroke with an ischemic core volume <50 cc) (see Table 5), the control group actually responded better than either of the dosage groups for those subjects with stroke volumes equal to or greater than 50 cc (see Table 6) or equal to or greater than 100 cc (see Table 7). These results indicate that DNTT-MSCs may be less effective for treating chronic stroke patients with ischemic core volumes greater than 50 cc.

Location of Stroke

Figure 5:
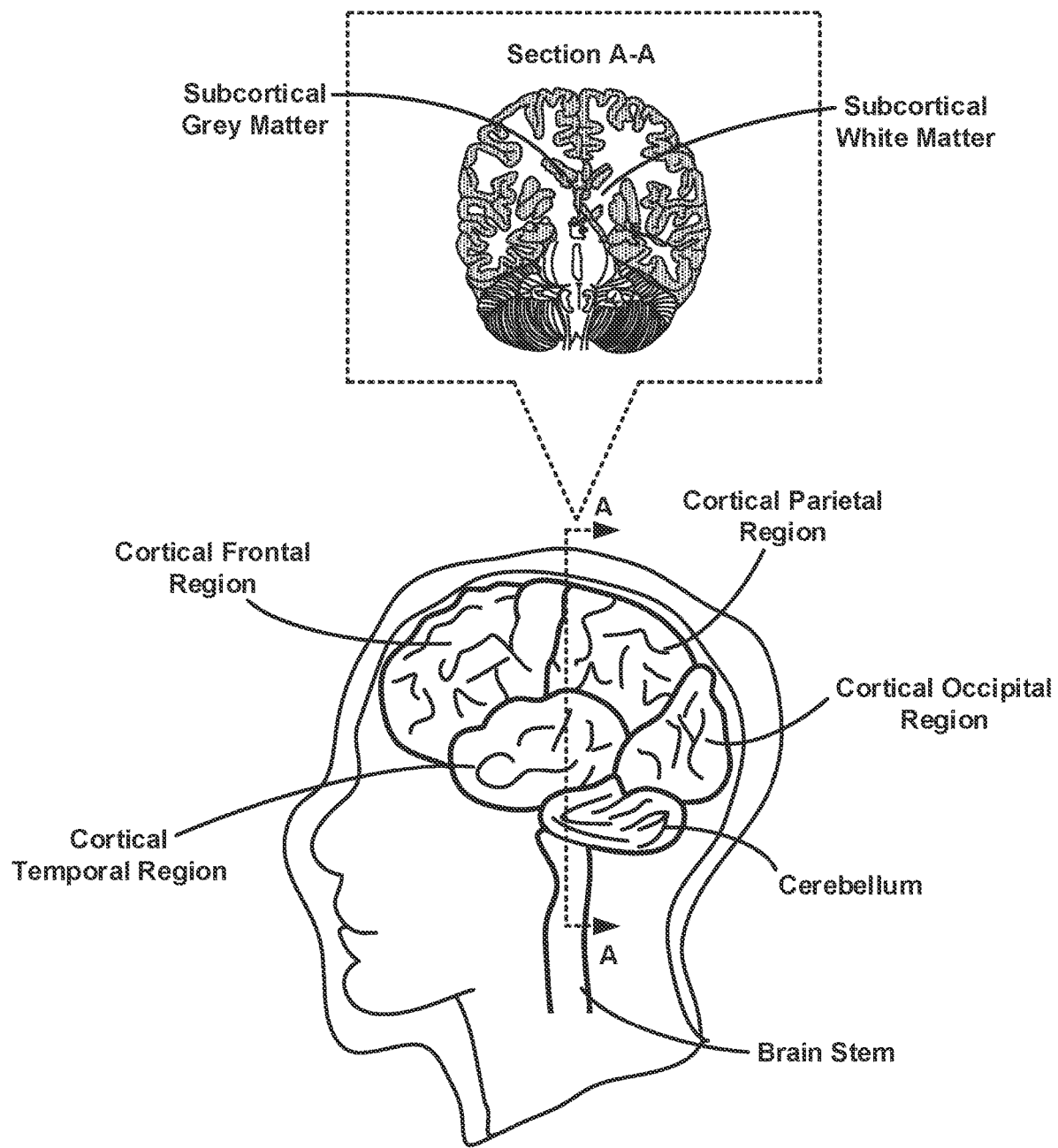
FIG. 5 illustrates various regions or areas of the brain including, among others, the subcortical white matter, the subcortical grey matter, the cortical frontal region, the cortical parietal region, and the cortical temporal region.

The retrospective analysis also examined the efficacy of the treatment based on the stroke location. Among the subject population, strokes (or, more aptly, the ischemic cores of such strokes) were recorded in the following regions/areas of the brain: (1) subcortical white matter, (2) subcortical grey matter, (3) cortical frontal region, (4) cortical parietal region, and (5) cortical temporal region. FIG. 5 illustrates these regions/areas of the brain along with other regions/areas of the brain.

As previously mentioned, one unexpected result discovered by the Applicant was that in subjects who had suffered a stroke in a region of the brain not in the cortical parietal region/lobe, a statistically significant difference (p-value=0.05) was observed in the proportion of subjects in the combined treatment group that exhibited clinically important improvements in their motor functioning compared to the sham/control group.

Moreover, yet another unexpected result discovered by the Applicant was that in subjects who had suffered a small-volume stroke (e.g., ischemic core volume <50 cc) in a region of the brain not in the cortical parietal region/lobe, an even greater statistically significant difference (p-value <0.01) was observed in the proportion of subjects in the combined treatment group that exhibited clinically important improvements in their motor functioning compared to the sham/control group.

Table 8 below shows the delta composite response rates and their accompanying p-values for the overall population and the subject population that did not suffer a stroke in their cortical parietal region.

TABLE 8

Delta composite response values and accompanying p-values for overall population and subjects who did not suffer a stroke in their cortical-parietal region at 24 weeks

| Group | Treatment Count | Treatment Composite Responders | Control Count | Control Composite Responders | Delta Composite Response Rate | p-value of Delta Composite Response Rate |
|---|---|---|---|---|---|---|
| Overall Population | 107 | 42 | 51 | 16 | 8% | 0.42 |
| No Stroke in Cortical Parietal Region | 62 | 26 | 21 | 4 | 23% | 0.05 |

Table 9 below shows various delta response rates and scores at 24 weeks for those in the small-volume stroke population (ischemic core volume <50 cc) who either suffered or did not suffer a stroke in their cortical parietal regions.

TABLE 9

Response rates and scores at 24 weeks for small-volume stroke population broken down by presence or absence of stroke in cortical parietal region.

| Stroke in Cortical Parietal | Treatment Count | Treatment Composite Response Rate | Control Count | Control Composite Response Rate | Delta Composite Response Rate | Avg. Baseline FMMS | Avg. Baseline mRS | Av. Vol. of Stroke |
|---|---|---|---|---|---|---|---|---|
| No | 40 | 52.5% | 15 | 6.7% | 45.8% (p-value < 0.01) | 47.95 | 2.71 | 11.59 |
| Yes | 11 | 36.4% | 11 | 36.4% | 0% | 51.09 | 2.45 | 23.42 |

As shown by Table 8 above, the subjects in the study population that did not suffer a stroke in their cortical parietal region had a significantly higher response rate (~42%) in the treatment arm in comparison to the control arm (~19%). The delta composite response rate of ~23% for this population subsegment was determined to be statistically significant (p-value=0.05) based on GLMM or logistic regression analysis.

Table 9 above shows that the best delta composite response rate (45.8%) was observed in the segment of the population with small-volume strokes (ischemic core volume <50 cc) who did not suffer a stroke in their cortical parietal region.

In view of these unexpected findings, administration of DNTT-MSCs may be considered an effective treatment for subjects suffering from chronic motor deficits caused by a ischemic stroke where the ischemic core was not located in the subjects' cortical parietal region. Moreover, administration of DNTT-MSCs may be an even more effective treatment for subjects suffering from chronic motor deficits caused by a small-volume ischemic stroke where the small-volume (core volume <50 cc) ischemic core was not located in the subjects' cortical parietal region.

FIG. 6 is a reference table generated as part of the retrospective analysis comprising information concerning the stroke location, baseline characteristics, and delta response rates of the study population broken down by population percentage.

Figure 7:
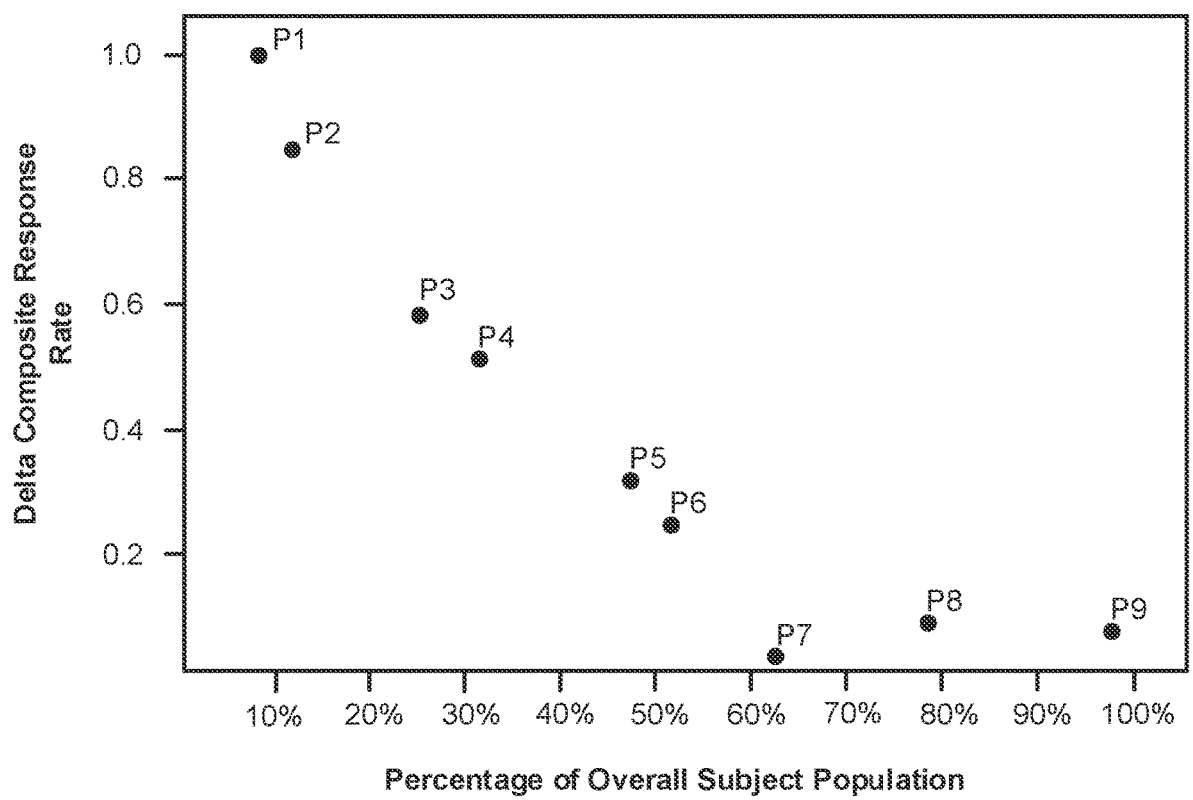
FIG. 7 is a plot showing the delta composite response rates of FIG. 6 plotted against the population percentages.

FIG. 7 is a plot showing the delta composite response rates of FIG. 6 plotted against the population percentages. As shown in FIG. 6, point P1 on the graph represents approximately 9% of the population and includes subjects with low stroke-volume (ischemic core volume <50 cc) and where the stroke did not occur in the subjects' subcortical grey matter or the cortical frontal region, point P2 on the graph represents approximately 11% of the population and includes subjects with low stroke-volume and where the stroke did not occur in the subjects' cortical parietal region, point P3 on the graph represents approximately 25% of the population and includes subjects with low stroke-volume and where the stroke did not occur in the subjects' cortical temporal region, point P4 on the graph represents approximately 31% of the population and includes subjects with low stroke-volume and where the stroke did not occur in either the cortical parietal region or the cortical temporal region, point P5 on the graph represents approximately 47% of the population and includes all study subjects with low stroke-volume (regardless of stroke location), point P6 on the graph represents approximately 51% of the population and includes all study subjects where the stroke did not occur in the subjects' cortical parietal region, point P7 on the graph represents approximately 63% of the population and includes all study subjects where the stroke occurred at least partly in the subjects' subcortical white matter, point P8 on the graph represents approximately 79% of the population and includes all study subjects who received cells processed in less than 180 minutes (considered a low cell processing time), and point P9 on the graph represents approximately 97% of the population (essentially, the entire study population).

FIGS. 6 and 7 illustrate that the population segments represented by points P5 (low stroke-volume) and P6 (no stroke in cortical parietal region) were the only two population segments where the response rates, including the delta composite response rate, were calculated from close to 50% of the total study population and both delta composite response rates were statistically significant.

It should also be noted that there is noticeable overlap between the P5 (low-stroke volume) and P6 (no stroke in cortical parietal region) populations as 55 out of the 83 subjects with no stroke in their cortical parietal regions also had low-volume strokes.

Progress of Composite Responders at 48 Weeks

In order to establish whether subjects who were W24 composite responders also showed improvement in their disability scores 24 weeks later (i.e., at 48 weeks or W48), clinical trial data at W48 was also analyzed for mRS CFB for the overall population and the subpopulation with low-stroke volume (ischemic core volume <50 cc).

Tables 10 and 11 below show W48 mRS changes for the overall population and the low-stroke volume subpopulation, respectively. It is important to note that a reduction in a subject's mRS is an improvement in the subject's degree of disability or disability level.

TABLE 10 mRS change of composite responders and non-responders in overall population at 48 weeks

| | Combined Treatment Group Count (n) | Control Group Count (n) | Combined Treatment Group W48 mRS CFB | Control Group W48 mRS CFB | Delta W48 mRS CFB |
|---|---|---|---|---|---|
| Composite Responders | 42 | 16 | −0.14 | 0.13 | −0.27 |
| Composite Non-Responders | 65 | 35 | −0.11 | −0.09 | −0.02 |

TABLE 11 mRS change of composite responders and non-responders in low-stroke volume subpopulation at 48 weeks

| | Combined Treatment Group Count (n) | Control Group Count (n) | Combined Treatment Group W48 mRS CFB | Control Group W48 mRS CFB | Delta W48 mRS CFB |
|---|---|---|---|---|---|
| Composite Responders | 25 | 5 | −0.20 | 0.20 | −0.40 |
| Composite Non-Responders | 26 | 21 | −0.12 | −0.10 | −0.02 |

As shown in Tables 10 and 11 above, composite responders in the low-stroke volume (ischemic core volume <50 cc) subpopulation exhibited better delta mRS CFB at 48 weeks than the overall population. Since improvement in a subject's motor response is a prerequisite to improvement in the subject's disability (this is known as the "lead lag effect"), the results show that the lead lag effect is present in composite responders in both the overall population and the low-stroke volume subpopulation at week 48 and the effect is more prominent in composite responders in the low-stroke volume subpopulation.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

REFERENCES

1. Johnson, Walter et al., Stroke: A global response is needed. *Bulletin of the World Health Organization.* September 2016; vol. 94(9): 634.
2. Engelstein E., Margulies J., and Jeret J. S. Lack of t-PA use for acute ischemic stroke in a community hospital: high incidence of exclusion criteria. *Am. J. Emerg. Med.* 2000; 18(3): 257-260.
3. Dobkin B. H. Strategies for stroke rehabilitation. *Lancet Neurol.* 2004; 3(9):528-536.
4. Bliss et al. Cell transplantation therapy for stroke. *Stroke.* 2007; 38 (Part 2): 817-826.
5. Kondziolka D., Wechsler L., and Achim C. Neural transplantation for stroke. *J Clin Neurosci.* 2002; 9(3): 225-230
6. Savitz et al. Cell therapy for stroke. *NeuroRx.* 2004; 1(4): 406-414.
7. Aizman I., Tirumalashetty B. J., McGrogan M., Case C. Comparison of the neuropoietic activity of gene-modified versus parental mesenchymal stromal cells and the identification of soluble and extracellular matrix-related neuropoietic mediators. *Stem Cell Res Ther.* 2014, 5:29.
8. Dao M., Tate C., McGrogan M., Case C. Comparing the angiogenic potency of naïve marrow stromal cells and Notch-transfected marrow stromal cells. *J Transl Med.* 2013, 11:81.
9. Aizman I., Tate C., McGrogan M., Case C. Extracellular matrix produced by bone marrow stromal cells and by their derivative, SB623 cells, supports neural cell growth. *J Neurosci Res.* 2009, 87: 3198-3206.
10. Fugl-Meyer et al. A method for evaluation of physical performance. *Scand J Rehabil Med.* 1975; 7(1): 13-31.
11. Campbell, Bruce C V, et al. Penumbral imaging and functional outcome in patients with anterior circulation ischaemic stroke treated with endovascular thrombectomy versus medical therapy: a meta-analysis of individual patient-level data. *The Lancet Neurology* 20191; 18(1): 46-55.
12. Fisher, Marc and Bastan, Birgul, Identifying and utilizing the ischemic penumbra. *Neurology* 2012; 79 (Suppl. 1): S79-S85.

I claim:

1. A method of treating a subject with a stroke-induced motor deficit, comprising:
    determining a volume of an ischemic core of the subject; and
    administering, to a brain region surrounding the ischemic core of the subject, a therapeutically effective amount of cells only when the volume of the ischemic core is determined to be less than 50 cubic centimeters (cc), wherein the cells are vandefitemcel, which are cells descended from mesenchymal stem cells transiently-transfected by a polynucleotide encoding a Notch intracellular domain (NICD).
2. The method of claim 1, further comprising administering, to the brain region surrounding the ischemic core of the subject, the therapeutically effective amount of cells only when the volume of the ischemic core is between about 2 cc and 50 cc.
3. The method of claim 1, wherein administering the therapeutically effective amount of the cells further comprises injecting at least part of a cell suspension comprising the cells at one or more deposit sites at an outer periphery of a chronic penumbra surrounding the ischemic core.
4. The method of claim 1, wherein administering the therapeutically effective amount of the cells further comprises injecting at least part of a cell suspension comprising the cells at one or more deposit sites proximal to or within a chronic penumbra surrounding the ischemic core.
5. The method of claim 1, wherein administering the therapeutically effective amount of the cells further comprises injecting at least part of a cell suspension comprising the cells at one or more deposit sites distal to a chronic penumbra surrounding the ischemic core.
6. The method of claim 1, wherein administering the therapeutically effective amount of the cells further comprises administering the therapeutically effective amount of the cells stereotactically via a single burr-hole craniostomy.

7. The method of claim 1, wherein the ischemic core is located in a region of the brain of the subject other than a parietal region.

8. The method of claim 1, wherein at least part of the ischemic core is located in at least one of a cortical frontal region, a cortical temporal region, a subcortical white matter, and a subcortical grey matter of the subject.

9. The method of claim 1, wherein the cells are made by a method comprising:
providing a culture of the mesenchymal stem cells;
contacting the culture of mesenchymal stem cells with the polynucleotide encoding the NICD, wherein the polynucleotide does not encode a full-length Notch protein,
selecting cells that comprise the polynucleotide; and
further culturing the selected cells in the absence of selection for the polynucleotide.

10. The method of claim 1, wherein the therapeutically effective amount of cells is approximately 2.5 million cells.

11. The method of claim 10, wherein administering the approximately 2.5 million cells comprises injecting a cell suspension comprising the cells at five deposit sites along a first deposit track, five deposit sites along a second deposit track, and five deposit sites along a third deposit track, wherein approximately 20-μL of the cell suspension is injected at each deposit site and wherein the cell suspension has a cell concentration of approximately $8.5*10^6$ cells/mL.

12. The method of claim 1, wherein the therapeutically effective amount of cells is approximately 5.0 million cells.

13. The method of claim 12, wherein administering the approximately 5.0 million cells comprises injecting a cell suspension comprising the cells at five deposit sites along a first deposit track, five deposit sites along a second deposit track, and five deposit sites along a third deposit track, wherein approximately 20-μL of the cell suspension is injected at each deposit site and wherein the cell suspension has a cell concentration of approximately $17.0*10^6$ cells/mL.

14. The method of claim 1, wherein the stroke-induced motor deficit is a result of an ischemic stroke suffered by the subject.

15. The method of claim 14, wherein the ischemic stroke occurred more than six months prior to administering the cells.

16. The method of claim 15, wherein the ischemic stroke occurred between six months and 90 months prior to administering the cells.

17. The method of claim 1, further comprising evaluating a degree of disability of the subject by determining an mRS score of the subject and administering the therapeutically effective amount of cells only when the mRS score of the subject is between 2 and 4.

18. The method of claim 1, wherein the mesenchymal stem cells are human bone marrow-derived cells.

19. The method of claim 1, wherein the therapeutically effective amount of cells are suspended in a sterile isotonic crystalloid solution.

20. The method of claim 1, further comprising subjecting a formulated dose of the cells to post-release testing prior to administering the cells to the subject.

\* \* \* \* \*